(12) United States Patent
Levine et al.

(10) Patent No.: US 10,718,732 B2
(45) Date of Patent: Jul. 21, 2020

(54) ACTIVE CMOS SENSOR ARRAY FOR ELECTROCHEMICAL BIOMOLECULAR DETECTION

(71) Applicant: The Trustees of Columbia University In The City Of New York, New York, NY (US)

(72) Inventors: Peter M. Levine, New York, NY (US); Kenneth L. Shepard, Ossining, NY (US); Ping Gong, Elmhurst, NY (US); Levicky Rastislav, Irvington, NY (US)

(73) Assignee: The Trustees Of Columbia University In The City of New York, New York, NY (US)

( * ) Notice: Subject to any disclaimer, the term of this patent is extended or adjusted under 35 U.S.C. 154(b) by 230 days.

(21) Appl. No.: 15/241,486

(22) Filed: Aug. 19, 2016

(65) Prior Publication Data

US 2017/0146479 A1    May 25, 2017

Related U.S. Application Data

(63) Continuation of application No. 12/819,720, filed on Jun. 21, 2010, now abandoned, which is a
(Continued)

(51) Int. Cl.
    *G01N 27/327*      (2006.01)
    *C12Q 1/682*      (2018.01)
    (Continued)

(52) U.S. Cl.
    CPC ....... *G01N 27/3277* (2013.01); *C12Q 1/6825* (2013.01); *G01N 27/48* (2013.01);
    (Continued)

(58) Field of Classification Search
    CPC .................................................. G01N 27/327
    See application file for complete search history.

(56) References Cited

U.S. PATENT DOCUMENTS 4,666,565 A    5/1987   Dobson
5,485,118 A    1/1996   Chick
(Continued)

FOREIGN PATENT DOCUMENTS

WO    WO 2004/061972 A1    7/2004
WO    WO 2010/123712 A1    10/2010

OTHER PUBLICATIONS

U.S. Appl. No. 09/591,270 (U.S. Pat. No. 7,103,522), filed Jun. 9, 2000 (Sep. 5, 2006).
(Continued)

*Primary Examiner* — Susan D Leong
(74) *Attorney, Agent, or Firm* — Hunton Andrews Kurth LLP

(57) ABSTRACT

Electrochemical sensing of biomolecules eliminates the need for bulky optical instruments required in traditional fluorescence-based sensing assays. Integration of the sensor interface electrodes and active electrochemical detection circuitry on CMOS substrates miniaturizes the sensing platform, enhancing portability for point-of-care applications, while enabling high-throughput, highly-parallel analysis. One embodiment includes a four-by-four active sensor array for multiplexed electrochemical biomolecular detection in a standard 0.25-μm CMOS process. Integrated potentiostats, including control amplifiers and dual-slope ADCs, stimulate the electrochemical cell and detect the current flowing through on-chip gold electrodes at each sensor site resulting from biomolecular reactions occurring on the chip surface. Post-processing techniques for fabricating biologically-compatible surface-electrode arrays in CMOS that can withstand operation in harsh electrochemical environments are
(Continued)

described. Demonstrations showing example operation of the active CMOS array for biomolecular detection include cyclic voltammetry of a reversible redox species, DNA probe density characterization, and quantitative and specific DNA hybridization detection in real time.

13 Claims, 25 Drawing Sheets

Related U.S. Application Data continuation of application No. PCT/US2008/087773, filed on Dec. 19, 2008.

(60) Provisional application No. 61/016,336, filed on Dec. 21, 2007.

(51) Int. Cl.
*C12Q 1/6825* (2018.01)
*G01N 27/48* (2006.01)
*H01L 23/522* (2006.01)
*H01L 23/528* (2006.01)
*H01L 23/532* (2006.01)

(52) U.S. Cl.
CPC ...... *H01L 23/5226* (2013.01); *H01L 23/5283* (2013.01); *H01L 23/53261* (2013.01)

(56) References Cited

U.S. PATENT DOCUMENTS

| | | | |
|---|---|---|---|
| 5,600,520 A | 2/1997 | Aokura et al. | |
| 5,612,698 A | 3/1997 | Reay | |
| 5,625,359 A * | 4/1997 | Wilson | H03M 3/372 341/123 |
| 5,837,392 A | 11/1998 | Katori et al. | |
| 5,952,893 A | 9/1999 | Ghoshal | |
| 6,023,577 A | 2/2000 | Smith, III et al. | |
| 6,100,694 A | 8/2000 | Wong | |
| 6,141,632 A | 10/2000 | Smith, III et al. | |
| 6,166,527 A | 12/2000 | Dwelley et al. | |
| 6,251,595 B1 * | 6/2001 | Gordon | B01J 19/0046 204/400 |
| 6,281,737 B1 | 8/2001 | Kuang et al. | |
| 6,362,986 B1 | 3/2002 | Schultz et al. | |
| 6,429,684 B1 | 8/2002 | Houston | |
| 6,442,735 B1 | 8/2002 | Joshi et al. | |
| 6,453,444 B1 | 9/2002 | Shepard et al. | |
| 6,490,546 B1 | 12/2002 | Kimmel et al. | |
| 6,567,773 B1 | 5/2003 | Rahmat et al. | |
| RE38,140 E | 6/2003 | Schaffer | |
| 6,643,913 B2 | 11/2003 | Uchikoba et al. | |
| 6,747,442 B2 | 6/2004 | Olsen et al. | |
| 6,784,644 B2 | 8/2004 | Xu et al. | |
| 6,900,643 B2 | 5/2005 | Deng et al. | |
| 7,103,522 B1 | 9/2006 | Shepard | |
| 7,140,092 B2 | 11/2006 | Park et al. | |
| 7,198,708 B2 | 4/2007 | Atkinson et al. | |
| 7,268,419 B2 | 9/2007 | Cornelius | |
| 7,300,757 B2 | 11/2007 | Edman et al. | |
| 7,300,803 B2 | 11/2007 | Lin et al. | |
| 7,345,464 B2 | 3/2008 | Steele | |
| 7,423,508 B2 | 9/2008 | Gardner et al. | |
| 7,482,792 B2 | 1/2009 | Burton et al. | |
| 7,567,444 B2 | 7/2009 | Chen et al. | |
| 7,649,434 B2 | 1/2010 | Xu et al. | |
| 7,667,441 B2 | 2/2010 | Muratov | |
| 7,670,889 B2 | 3/2010 | Pekarik et al. | |
| 7,688,607 B2 | 3/2010 | Schultz | |
| 7,777,459 B2 | 8/2010 | Williams | |
| 7,843,302 B2 | 11/2010 | Mano et al. | |
| 7,852,185 B2 | 12/2010 | Gardner et al. | |
| 7,928,550 B2 | 4/2011 | Wachtler | |
| 7,943,445 B2 | 5/2011 | Anderson et al. | |
| 8,102,236 B1 | 1/2012 | Fontana, Jr. et al. | |
| 8,270,137 B2 | 9/2012 | Briere et al. | |
| 8,471,358 B2 | 6/2013 | Yen et al. | |
| 8,610,247 B2 | 12/2013 | Yen et al. | |
| 8,716,855 B2 | 5/2014 | Chi et al. | |
| 8,823,133 B2 | 9/2014 | Jenkins et al. | |
| 8,866,258 B2 | 10/2014 | Xia et al. | |
| 9,048,233 B2 | 6/2015 | Wu et al. | |
| 9,324,489 B2 | 4/2016 | Fontana, Jr. et al. | |
| 9,330,823 B1 | 5/2016 | Rahman et al. | |
| 2002/0195662 A1 | 12/2002 | Eden et al. | |
| 2003/0078763 A1 | 4/2003 | Chuang et al. | |
| 2003/0160675 A1 | 8/2003 | Von Der et al. | |
| 2004/0036452 A1 | 2/2004 | Brooks | |
| 2004/0046535 A1 | 3/2004 | Duffy et al. | |
| 2005/0040800 A1 | 2/2005 | Sutardja | |
| 2006/0113922 A1 | 6/2006 | Ribarich et al. | |
| 2006/0115684 A1 | 6/2006 | Choi | |
| 2006/0115857 A1 * | 6/2006 | Keen | B82Y 10/00 435/7.1 |
| 2006/0152324 A1 | 7/2006 | Haugs et al. | |
| 2006/0172279 A1 | 8/2006 | Smela et al. | |
| 2006/0181228 A1 | 8/2006 | Sanchez-Olea | |
| 2006/0192536 A1 | 8/2006 | Chen et al. | |
| 2007/0080060 A1 | 4/2007 | Frey et al. | |
| 2007/0142718 A1 | 6/2007 | Abreu | |
| 2007/0159325 A1 * | 7/2007 | Oleynik | G01N 33/5438 340/539.26 |
| 2007/0212596 A1 | 9/2007 | Nebrigic et al. | |
| 2007/0229192 A1 | 10/2007 | Miura et al. | |
| 2008/0048631 A1 | 2/2008 | Kim | |
| 2008/0073225 A1 | 3/2008 | Paulus | |
| 2008/0075975 A1 | 3/2008 | Glaser et al. | |
| 2008/0158915 A1 | 7/2008 | Williams | |
| 2008/0246571 A1 | 10/2008 | Guenther | |
| 2008/0272408 A1 | 11/2008 | Vora | |
| 2008/0297292 A1 | 12/2008 | Viala et al. | |
| 2009/0094818 A1 | 4/2009 | Smeys et al. | |
| 2009/0290442 A1 | 11/2009 | Rajan | |
| 2009/0322296 A1 | 12/2009 | Li et al. | |
| 2010/0033288 A1 | 2/2010 | Yokoyama et al. | |
| 2011/0067236 A1 | 3/2011 | Muthukumar et al. | |
| 2011/0111559 A1 | 5/2011 | Mitchell et al. | |
| 2011/0291193 A1 | 12/2011 | Bryant et al. | |
| 2012/0146756 A1 | 6/2012 | Roellgen et al. | |
| 2012/0243279 A1 | 9/2012 | Zacharias et al. | |
| 2012/0274366 A1 | 11/2012 | Briere | |
| 2013/0106552 A1 | 5/2013 | Fontana, Jr. et al. | |
| 2013/0154582 A1 | 6/2013 | Draese et al. | |
| 2014/0092574 A1 | 4/2014 | Zillmann et al. | |
| 2014/0239924 A1 | 8/2014 | Guo | |
| 2014/0320104 A1 | 10/2014 | Guo | |
| 2015/0054573 A1 | 2/2015 | Zhou et al. | |

OTHER PUBLICATIONS

U.S. Appl. No. 09/496,805 (U.S. Pat. No. 6,453,444), filed Feb. 2, 2000 (Sep. 17, 2002).
U.S. Appl. No. 12/819,720 (Abandoned), filed Jun. 21, 2010.
U.S. Appl. No. 14/094,080 (US 2014/0167898), filed Dec. 2, 2013 (Jun. 19, 2014).
U.S. Appl. No. 14/172,210 (US 2014/0152278), filed Feb. 4, 2014 (Jun. 5, 2014).
U.S. Appl. No. 14/333,427 (US 2015/0042400), filed Jul. 16, 2014 (Feb. 12, 2015).
U.S. Appl. No. 09/591,270, Jul. 3, 2006 Issue Fee payment.
U.S. Appl. No. 09/591,270, Jun. 16, 2006 Notice of Allowance.
U.S. Appl. No. 09/591,270, Feb. 28, 2006 Response to Non-Final Office Action.
U.S. Appl. No. 09/591,270, Feb. 6, 2006 Non-Final Office Action.
U.S. Appl. No. 09/591,270, Mar. 31, 2005 Request for Continued Examination (RCE).
U.S. Appl. No. 09/591,270, Mar. 14, 2005 Advisory Action.
U.S. Appl. No. 09/591,270, 2/3/205 Response to Final Office Action.

(56) References Cited

OTHER PUBLICATIONS

U.S. Appl. No. 09/591,270, Sep. 30, 2004 Final Office Action.
U.S. Appl. No. 09/591,270, Jun. 28, 2004 Response to Non-Final Office Action.
U.S. Appl. No. 09/591,270, Aug. 4, 2003 Non-Final Office Action.
U.S. Appl. No. 09/496,805, Jul. 30, 2002 Issue Fee payment.
U.S. Appl. No. 09/496,805, May 7, 2002 Notice of Allowance.
U.S. Appl. No. 09/496,805, Mar. 12, 2002 Response to Non-Final Office Action.
U.S. Appl. No. 09/496,805, Nov. 5, 2001 Non-Final Office Action.
Allan, et al., "WP 25.7 A 0.2µm 1.8V SOI 550MHz 64b PowerPC Microprocessor with Copper Interconnects", IEEE International Solid-State Circuits Conference, 438-439 (1999).
Augustyniak, "A 24X16 Cmos-Based Chronocoulometric Dna Microarray", IEEE Journal of Solid-State Circuit Conference Digest of Technical Papers, pp. 59-68 (2006).
Caillat, et al., "Biochips on CMOS: An Active Matrix Address Array for DNA Analysis", Sensors and Actuators B: Chemical, 61(1-3):154-162 (1999).
Chang, et al., "A Fully-Integrated Switched-Capacitor 2:1 Voltage Converter with Regulation Capability and 90% Efficiency at 2.3A/mm2", Symposium on VLSI circuits/technical digest of Technical Papers, pp. 55-56 (2010).
Chuang, "Design Considerations of SOI Digital CMOS VLSI", Proceedings IEEE International SOI Conference, pp. 5-8 (1998).
Chuang, et al., "Design Considerations of Scaled sub-0.1/spl mu/m PD/SOI CMOS Circuits", Proceedings Fourth International Symposium on Quality Electronic Design, pp. 153-158 (Mar. 24-26, 2003).
Frommberger, "Integration of Crossed Anistrop Magnetic Core Into Toroidal Thin-Film Inductors", IEEE Transaction on Microwave Theory and Techniques, 53(6):2096-2099 (2005).
Gemma, et al., "CMOS Integrated DNA Chip for Quantitative DNA Analysis", IEEE International Solid-State Circuits Conference Digest of Technical Papers, pp. 560-561 (2006).
Hassibi, et al., "A Programmable 0.18-µm CMOS Electrochemical Sensor Microarray for Biomolecular Detection", IEEE Sensors Journal, 6(6):1380-1388 (2006).
Hazucha, et al., "A 233-MHz 80%-87% Efficient Four-Phase DC-DC Converter Utilizing Air-Core Inductors on Package", IEEE Journal of Solid-State Circuits, 40(4):838-845 (2005).
International Conference on Computer-Aided Design, Nov. 7-11, 1999, San Jose, CA, USA, ACM 1999 http://informatik.uni-trier.de/-ley/db/conf/iccas1999.html. Printed Feb. 18, 2004.
International Search Report and Written Opinion for PCT/US2013/065478, dated Mar. 19, 2014.
International Search Report for PCT/US08/87773, dated Feb. 19, 2009 (Corresponds to U.S. Appl. No. 12/819,720).
International Search Report for PCT/US2012/040147, dated Aug. 17, 2012.
International Search Report for PCT/US2012/051532, dated Nov. 2, 2012.
International Search Report for PCT/US2013/022145, dated May 21, 2013.
Le, et al., "A 32nm Fully Integrated Reconfigurable Switched-Capacitor DC-DC Converter Delivering 0.55W/mm2 at 81% Efficiency", IEEE International Solid-State Circuits Conference, pp. 209-211 (2010).
Lu, et al., "Floating-Body Effects in Partially Depleted SOI CMOS Circuits", IEEE Journal of Solid-State Circuits, 32(8):1241-1253 (1997).
Martin, "A CMOS-Integrated Microinstrument for Trace Detection of Heavy Metals", IEEE Journal of Solid-State Circuits, 40(12):2777-2786 (2005).
Puri, et al., "Histeresis Effect in Pass-Transistor Based Partially-Depleted SOI CMOS Circuits", Proceedings IEEE International SOI Conference, pp. 103-104 (1998).
Puri, et al., "SOI Digital Circuits: Design Issues", 13th International Conference on VLSI Design, pp. 474-479 (Jan. 3-7, 2000).

Schienle, et al., "A Fully Electronic DNA Sensor with 128 Positions and In-Pixel A/D Conversion", IEEE Journal of Solid-State Circuits, 39(12):2438-2445 (2004).
Schrom, et al., "A 100MHz Eight-Phase Buck Converter Delivering 12A in 25mm2 Using Air-Core Inductors", Twenty Second Annual IEEE Applied Power Electronics Conference, PAEC 2007, pp. 727-730 (2007).
Schrom, et al., "A 480-MHz, Multi-Phase Interleaved Buck DC-DC Converter with Hysteretic Control", 2004 35th Annual IEEE Power Electronics Specialist Conference, pp. 4702-4707 (2004).
Shepard "Static Noise Analysis for Digital Integrated Circuits in Partially-Depleted Silicon-On_Insulator Technology", Proc. 37th ACM/IEEE DSC, pp. 239-242 (2000).
Shepard, "Design Methodologies for Noise in Digital Integrated Circuits", Annual ACM/IEEE Design Automation Conference, pp. 94-99 (1998).
Shepard, et al., "Body-Voltage Estimation in Digital PD-SOI Circuits and its Application to Static Timing Analysis", IEEE/ACM International Conference on CAD, pp. 531-538 (Nov. 7-11, 1999).
Shepard, et al., "Harmony: Static Noise Analysis of Deep Submicron Digital Integrated Circuits", IEEE Transactions on CAD of Integrated Circuits and Systems, 18(8):1132-1150 (1999).
Shi, et al., "A Cost-Competitive High Performance Junction-FET (JFET) in CMOS Process for RF and Analog Applications", IEEE Radio Frequency Integrated Circuits Symposium, pp. 237-240 (2010).
Sinitsky, et al., "Simulation of SOI Devices and Circuits Using BSIM3SOI", Electron Device Letters, IEEE, 19(9):323-325 (1998).
Stagni, "MOS DNA Sensor Array with Integrated a/D Conversion Based on Label-Free Capacitance Measurement", IEEE Journal of Solid-State Circuits, 41(12):2956-2964 (2006).
Takao, et al., "A JFET-CMOS Technology for Low-Noise Sensor Interface Circuits", IEEJ Transactions on Sensors and Micromachines, 123(10):422-428 (2003).
Takao, et al., "Low-Noise Fullt Differential amplifiers Using JFET-CMOS Integration Technology for smart Sensors", IEEJ Transactions on Electrical and Electronic Engineering, 3(3):274-280 (2008).
Tu, et al., "Simulation of Floating Body Effect in SOI Circuits Using BSIM3SOI", VLSI Technology, Systems, and Applications, International Symposium on Proceedings of Technical Papers, pp. 339-342 (Jun. 3-5, 1997).
Wei, "Transient Behavior of the Kink Effect in Partially-Depleted SOI MOSFET' s", IEEE Electron Device Letters, 16(11):494-499 (1995).
U.S. Appl. No. 12/819,720, Nov. 17, 2016 Notice of Abandonment.
U.S. Appl. No. 12/819,720, Apr. 5, 2016 Non-Final Office Action.
U.S. Appl. No. 12/819,720, Jan. 4, 2016 Amendment and Request for Continued Examination (RCE).
U.S. Appl. No. 12/819,720, Aug. 3, 2015 Final Office Action.
U.S. Appl. No. 12/819,720, Apr. 21, 2015 Response to Non-Final Office Action.
U.S. Appl. No. 12/819,720, Oct. 22, 2014 Non-Final Office Action.
U.S. Appl. No. 12/819,720, Apr. 1, 2014 Amendment and Request for Continued Examination (RCE).
U.S. Appl. No. 12/819,720, Mar. 28, 2014 Applicant Initiated Interview Summary.
U.S. Appl. No. 12/819,720, Oct. 10, 2013 Final Office Action.
U.S. Appl. No. 12/819,720, Jul. 23, 2013 Response to Non-Final Office Action.
U.S. Appl. No. 12/819,720, Mar. 26, 2013 Non-Final Office Action.
U.S. Appl. No. 12/819,720, Feb. 25, 2013 Applicant Initiated Interview Summary.
U.S. Appl. No. 12/819,720, Feb. 14, 2013 Response to Restriction Requirement.
U.S. Appl. No. 12/819,720, Sep. 14, 2012 Restriction Requirement.
U.S. Appl. No. 14/094,080, Jan. 30, 2017 Final Office Action.
U.S. Appl. No. 14/094,080, Nov. 9, 2016 Response to Non-Final Office Action.
U.S. Appl. No. 14/094,080, Aug. 10, 2016 Non-Final Office Action.
U.S. Appl. No. 14/172,210, Jul. 6, 2016 Notice of Abandonment.
U.S. Appl. No. 14/172,210, Mar. 14, 2016 Notice of Allowance.
U.S. Appl. No. 14/172,210, Feb. 9, 2016 Response to Non-Final Office Action.

(56) References Cited

OTHER PUBLICATIONS

U.S. Appl. No. 14/172,210, Nov. 18, 2015 Non-Final Office Action.
U.S. Appl. No. 14/333,427, Feb. 16, 2017 Final Office Action.
U.S. Appl. No. 14/333,427, Feb. 6, 2017 Response after Final Office Action.
U.S. Appl. No. 14/333,427, Nov. 4, 2016 Final Office Action.
U.S. Appl. No. 14/333,427, Aug. 16, 2016 Response to Non-Final Office Action.
U.S. Appl. No. 14/333,427, Apr. 20, 2016 Non-Final Office Action.
U.S. Appl. No. 14/333,427 Mar. 4, 2016 Response to Restriction Requirement.
U.S. Appl. No. 14/333,427, Nov. 5, 2015 Restriction Requirement.

* cited by examiner image# ACTIVE CMOS SENSOR ARRAY FOR ELECTROCHEMICAL BIOMOLECULAR DETECTION

CROSS REFERENCE TO RELATED APPLICATIONS

This application is a continuation of U.S. patent application Ser. No. 12/819,720, filed Jun. 21, 2010, which is a continuation of International Patent Application Serial No. PCT/US2008/087773, filed on Dec. 18, 2008, which claims priority to U.S. Provisional Patent Application Ser. No. 61/016,336, filed on Dec. 21, 2007. The entireties of the disclosures of the foregoing applications are explicitly incorporated by reference herein.

STATEMENT REGARDING FEDERALLY SPONSORED RESEARCH

This invention was made with government support under grant HG003089 awarded by the National Institutes of Health. The Government has certain rights in this invention.

BACKGROUND

Quantitative and specific detection of biomolecules such as DNA and proteins have a wide variety of applications, for example, in biomedical diagnostics and environmental monitoring. DNA sensing has broad application, for example, in genotyping, gene-expression studies, mutation detection, pharmacogenomics, forensics, and related fields in which genetic contents provide insight into biological function or identity. Multiplexed DNA analysis can be performed in a laboratory environment using a "microarray", a passive substrate (such as a glass slide) on which thousands of single-stranded DNA (ssDNA) "probe" molecules arranged in a regular pattern bind to (or "hybridize" with) fluorophore-labeled "target" molecules in an analyte solution. Probes can be synthesized externally and then immobilized on the microarray through mechanical contact spotting or non-contact ink-jet printing, or can be constructed in situ using photolithographic techniques and solid-phase chemical synthesis. Hybridization occurs, for example, when the probe and target sequences are complementary to one another. Microarray scanners, employing laser sources that excite the fluorophores and photomultiplier tubes or CCD cameras that detect the emitted light, can measure surface-bound target densities down to $10^6$ cm$^{-2}$. Relative expression levels of bound targets at different array sites can then be quantified from the resulting image. However, fluorescent techniques typically require labeled targets and bulky instrumentation, making them ill-suited for point-of-care applications.

Electrochemical sensing approaches to DNA detection rely on detecting changes occurring with hybridization at the interface between a metal "working" electrode ("WE"), functionalized with probe molecules, and a conductive target analyte solution. One example feedback circuit known as a "potentiostat" can be used to apply a desired potential across the WE interface and measure the resulting current. If the target molecules are conjugated, for example, with "redox" labels (e.g., chemical species which gain electrons (undergo reduction) or lose electrons (undergo oxidation) due to an applied potential), probe-target binding can be detected, for example, by measuring changes in the direct (Faradaic) current flowing across the interface. Alternatively, label-free sensing can be performed, for example, by measuring changes in displacement (non-Faradaic) current at the interface that occur due to surface-charge fluctuations.

Microarray applications based on electrochemical sensing often require parallel detection of hundreds to thousands of sensing sites. This requires active multiplexing that can be achieved through integration of the WEs onto an active complementary metal-oxide-semiconductor ("CMOS") substrate containing the sensor electronics.

FIGS. 24a-c depict several sensor chip architectures. FIG. 24a depicts a sensor chip interfaced with one off-chip working electrode. FIG. 24b depicts an array of on-chip sensing elements connected individually to off-chip working electrodes. FIG. 24c depicts the integration of arrays of sensing elements with on-chip working electrodes, where all electrochemical reactions are carried out on the sensor chip surface.

A need exists for a technique which supports generalized potentiostat functionality and real-time monitoring of hybridization with the ability to directly measure surface target coverages.

SUMMARY

Devices and techniques for electrochemical biomolecular detection using an active CMOS sensor array are described.

The present subject matter includes devices and techniques for quantitative, real-time detection of DNA hybridization using active CMOS-integrated electrochemical microarrays. In some embodiments, the disclosed subject matter includes an array of generalized high-performance feedback control devices. The array can include one or more working electrodes, local controllers, signal converters, counter electrodes, and control amplifiers. The array can also include one or more reference electrodes, be controlled by a global controller and further connected to a clock generator and a digital counter.

Techniques for forming an array of generalized high-performance feedback control devices are also presented. In some embodiments, a technique includes integrating one or more working electrodes, local controllers, signal converters, counter electrodes, and control amplifiers. The formed arrays can be cleaned and packaged with protective packaging.

Techniques for operating an array of generalized high-performance feedback control devices are also described. An electrochemical measurement technique, for example a cyclic voltammetry technique, can be employed, and can include stimulating an electrochemical cell formed from a substance occurring on the surface of the array, and measuring the reactions, or stimulating and measuring electrochemical reactions of a biological substance on the surface of the array. The array can be implemented in a CMOS process.

The presently disclosed subject matter also provides devices for electrochemical sensing of biomolecules, including an integrated circuit. The devices can include one or more working electrodes on the integrated circuit, the one or more working electrodes configured to receive one or more biomolecular probes, a desired potential maintained through one or more reference electrodes, the one or more working electrodes configured to form a portion of one or more corresponding potentiostats, and a digitizing circuit on the integrated circuit configured to measure a signal indicative of a biomolecule sensing operation in real time. In some embodiments, the integrated circuit can include a complementary metal-oxide-semiconductor (CMOS) chip having a top metal layer operably connected to one or more vias for routing electrical signals. In some embodiments, the chip can be fabricated in a 2.5-V, 5-metal, 0.25-μm CMOS process. The one or more working electrodes can include square, gold electrodes. The one or more working electrodes can be adhered to the top metal layer with an adhesion layer. The adhesion layer can include titanium. The digitizing circuit can include a dual-slope analog-to-digital converter circuit. The one or more working electrodes can be in contact with an electrolyte solution, and the electrolyte solution can include one or more target molecules.

Other embodiments can include techniques for electrochemical sensing of biomolecules including providing one or more working electrodes on an integrated circuit, a desired potential maintained through one or more reference electrodes, the one or more working electrodes configured to bind one or more biomolecular probes, the one or more working electrodes configured to form a portion of one or more corresponding potentiostats, and providing a digitizing circuit on the integrated circuit configured to receive a signal resulting from an electrochemical measurement operation to measure one or more aspects of a biomolecular reaction in real time. The techniques can further include binding one or more biomolecular probes at the one or more working electrodes. The electrochemical measurement operation can include cyclic voltammetry, linear-sweep voltammetry, square-wave voltammetry, ac voltammetry, ac impedance, or electrochemical impedance spectroscopy techniques. The techniques can further include analyzing the biomolecular reaction to quantify surface target coverages. The biomolecular reaction can be indicative of quantitative and specific detection of biomolecules. The biomolecular reaction can be indicative of DNA sensing.

Further embodiments include techniques for manufacturing a CMOS-based array for electrochemically measuring a biomolecular reaction. The techniques can include defining one or more openings in a passivation layer of a CMOS chip to expose a top metal layer, depositing an adhesion layer at one of the openings, the adhesion layer in electrical communication with the top metal layer, depositing a metal layer on the adhesion layer to form a working electrode at at least one of the openings, the working electrode in electrical communication with the adhesion layer, the working electrode configured to bind one or more biomolecular probes, the working electrode configured to form a portion of a potentiostat, and electrically connecting an on-chip digitizing circuit to the working electrode, the digitizing circuit configured to measure an electrical signal resulting from the biomolecular reaction. Defining the one or more openings can include using a wet etch process to selectively remove the top metal layer. The deposition of the adhesion layer can include an electron-beam deposition procedure. The techniques can further include encapsulating bond wires in a chemically resistant epoxy to shield the wires from exposure to an electrolyte. A layer of polydimethylsiloxane can be included between the chip and a top plate, the polydimethylsiloxane layer preventing leakage of the electrolyte. Further techniques can include forming a reservoir above the chip to hold the electrolyte.

Some embodiments include techniques for electrochemical sensing of biomolecules including means for binding one or more biomolecular probes at one or more working electrodes of an integrated circuit, the integrated circuit including one or more working electrodes, a desired potential maintained through one or more reference electrodes, and a digitizing circuit on the integrated circuit configured to measure a signal indicative of a biomolecule sensing operation in real time, the one or more working electrodes configured to form a portion of one or more corresponding potentiostats, and means for performing an electrochemical measurement operation to measure one or more aspects of a biomolecular reaction in real time.

DETAILED DESCRIPTION

Active CMOS electrochemical sensor arrays for biomolecular detection can eliminate the need for the bulky and expensive optical equipment used in fluorescence-based microarrays. Such a reduction in size and complexity paves the way for the use of electrochemical microarrays in point-of-care applications. In some example embodiments, the design of a four-by-four array implemented in a standard 0.25-μm CMOS process augmented by post-processing to fabricate integrated electrochemically-compatible and biologically-compatible electrodes is employed. Integrated potentiostat electronics and ADCs stimulate and measure electrochemical reactions occurring at the chip surface. Results from demonstrations of cyclic voltammetry measurements of redox species, characterization of DNA probe coverages, and quantitative and specific detection of DNA probe-target hybridization illustrate some bio-diagnostic capabilities of the chip.

In one embodiment, a potentiostat is, for example, a feedback control device used to apply a desired potential to an electrochemical cell and simultaneously measure the movement of charge through the cell that accompanies electrochemical reactions occurring at an electrode-electrolyte interface. One example potentiostat 200 used in a typical electrochemical setup, shown conceptually in FIG. 1, includes three electrodes immersed in an electrolyte: a WE 202 at which the reaction of interest occurs and to which biomolecular probes can be attached, a "reference" electrode (RE) 204 to hold the electrolyte at a known potential, and a "counter" electrode (CE) 206. The voltage V between WE 202 and CE 206 is adjusted to establish a desired cell input voltage $V_{in}$ between the WE 202 and RE 204. Direct current (I) can flow through the external circuit as measured by the ammeter (A) 210 as soluble redox species in the electrolyte, for example, donate electrons to the WE 202 and accept electrons from the CE 206 (through a "Faradaic" process). Conversely, a charging (displacement) current can flow as ions segregate to the WE 202 and CE 206 to form space-charge regions (through a "non-Faradaic" process). The high-impedance voltmeter 208 attached to the RE 204 ensures that very low current flows through this interface, helping to maintain it at equilibrium.

Figure 1:
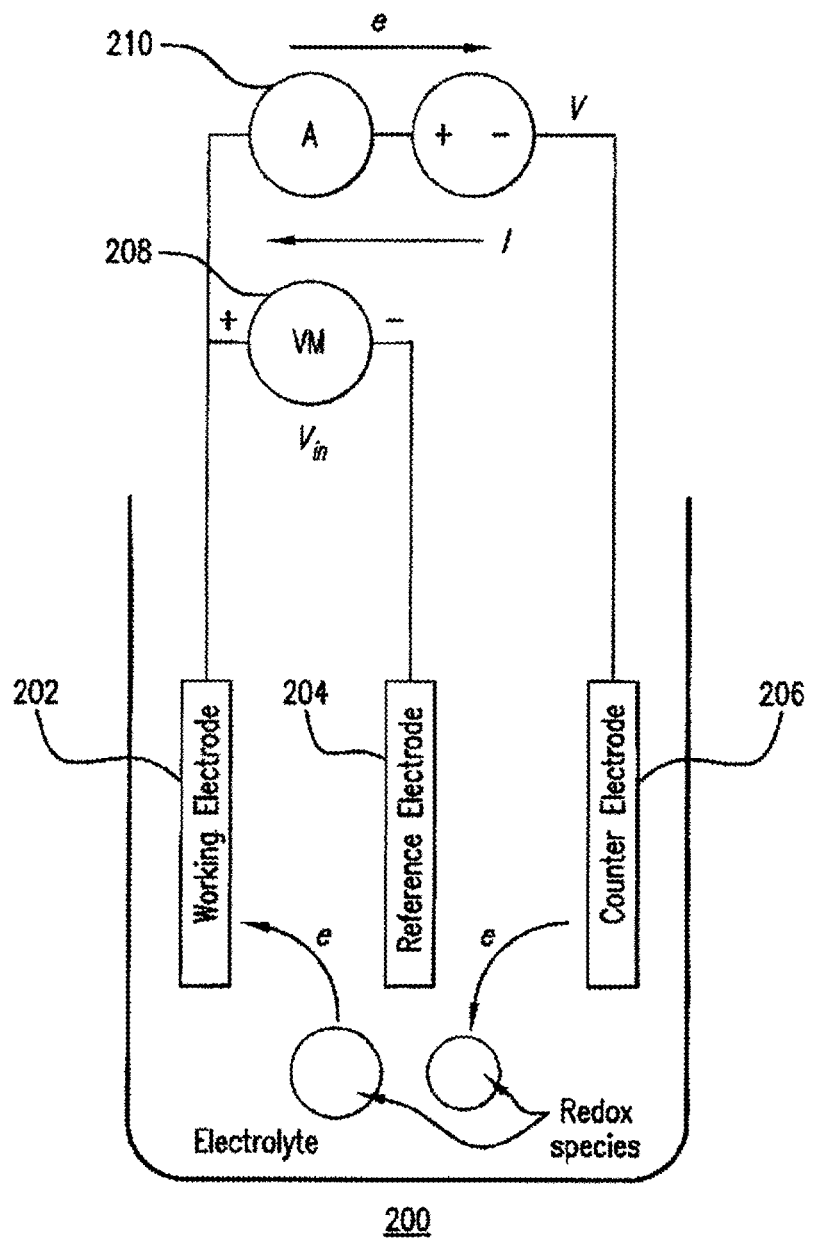
FIG. 1 shows a potentiostat according to one embodiment of the disclosed subject matter.
Figure 2:
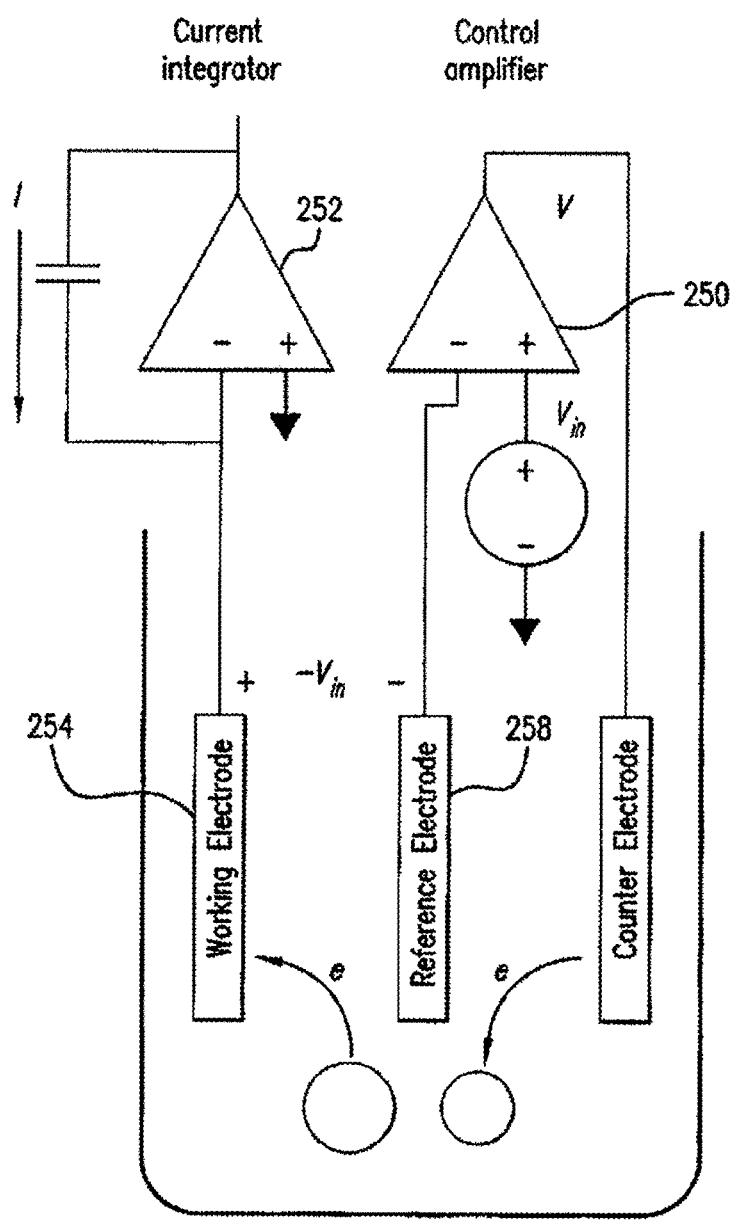
FIG. 2 shows a potentiostat according to one embodiment of the disclosed subject matter.

The exemplary potentiostat circuitry in FIG. 1 can be implemented in one embodiment using standard electronic components as shown in FIG. 2. The control amplifier implemented as an operational amplifier (op amp) or operational transconductance amplifier (OTA) 250 on the right establishes the control loop while the integrator 252 on the left converts the current flowing through the WE 254 to a voltage for digitization and readout. The high input impedance of the control amplifier 250 ensures that a very small current flows through the RE 258. This circuit can be implemented in a CMOS process and forms the basis of the exemplary integrated sensor array 260.

Figure 3:
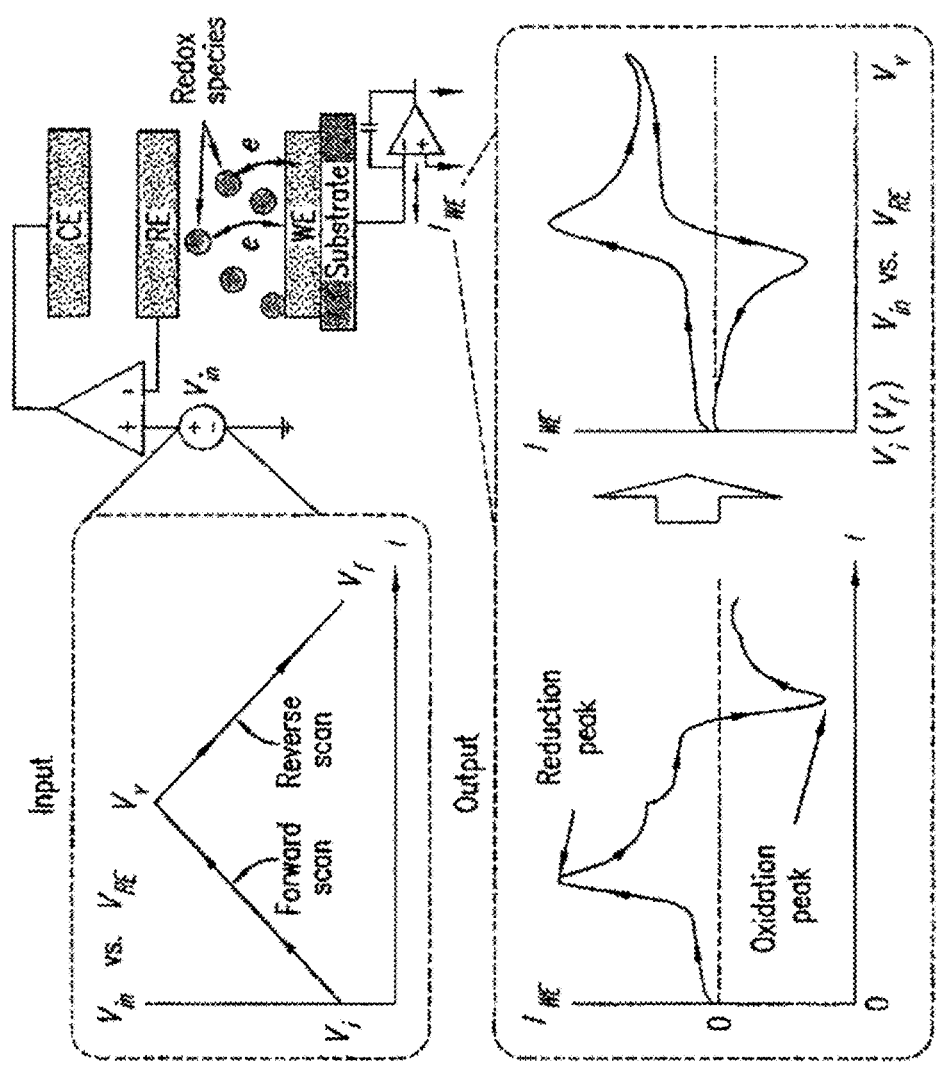
FIG. 3 depicts an illustration in accordance with an exemplary embodiment of the disclosed subject matter.

Different sensing modalities are determined by the nature of the input voltage applied to the potentiostat. Examples include linear-sweep voltammetry, cyclic voltammetry, square-wave voltammetry, anodic stripping voltammetry, chronoamperometry, chronocoulometry, and electrochemical impedance spectroscopy. In some embodiments, cyclic voltammetry (CV), a low-speed, large-signal technique, is used to detect redox species, determine surface DNA probe concentration, and measure DNA probe-target hybridization is used. In CV, $V_{in}$ (e.g., expressed relative to a standard RE potential, denoted here as $V_{RE}$) is set to the initial voltage $V_i$, ramped up to the vertex potential $V_v$, at the scan rate v, and then ramped down at the same rate until the final voltage $V_f$ (usually equal to $V_i$) is reached, as shown in FIG. 3 (measurement of an electrochemical cell containing a redox species in solution using CV), while the current flowing through the WE $i_{WE}$ is measured simultaneously. When detecting redox species present in solution, $i_{WE}$ as a function of time would appear as shown in the figure. In some embodiments, $i_{WE}$ is viewed as a function of $V_{in}$ so that the potentials at which reduction or oxidation occur (indicated by the forward and reverse current peaks, respectively) can be easily discerned. These potentials, as well as the value of $i_{WE}$ at each peak, indicate the degree of reversibility of the electrochemical reaction as well as the amount of chemical product generated or reactant consumed.

Figure 15:
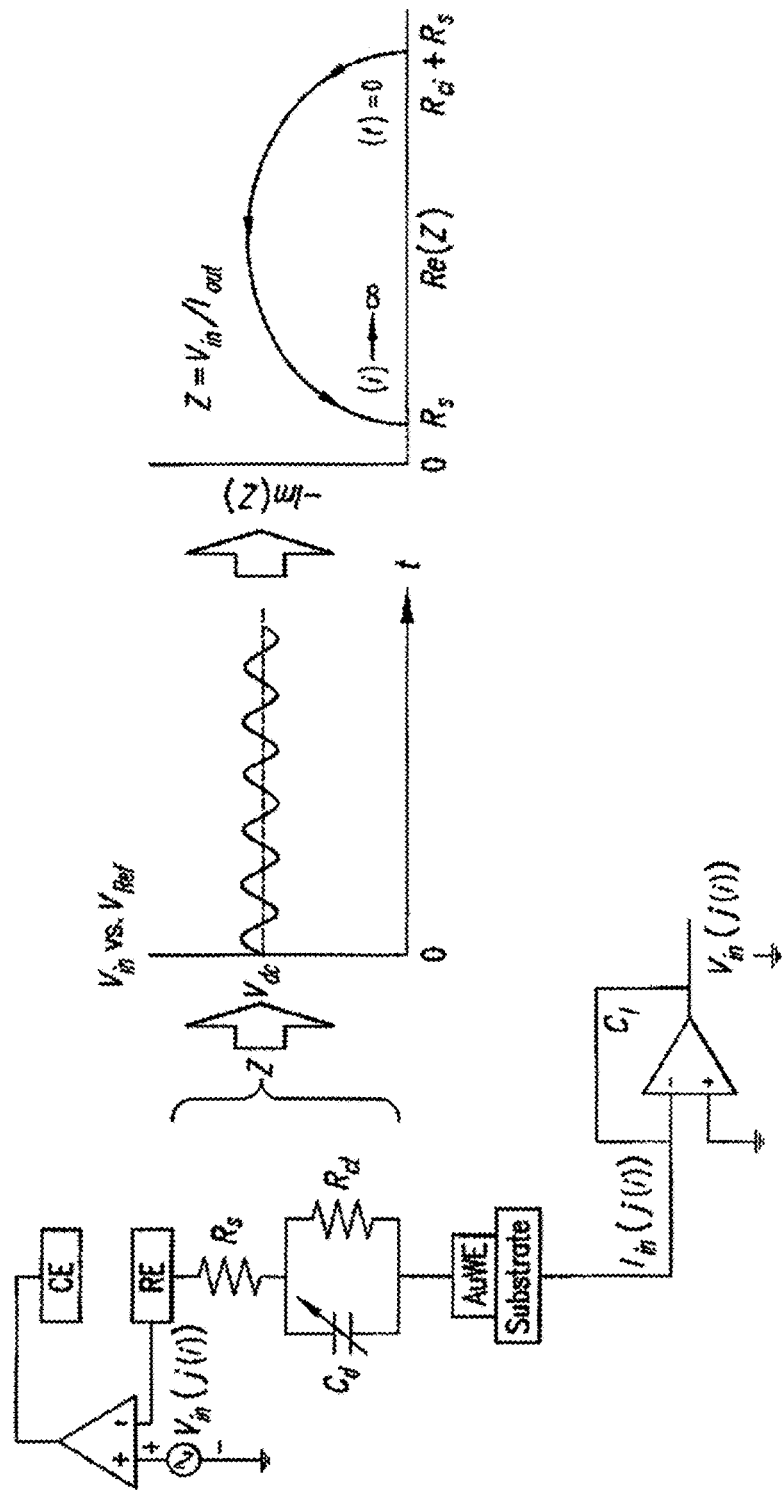
FIG. 15 depicts results according to an exemplary embodiment of the disclosed subject matter.
Figure 16:
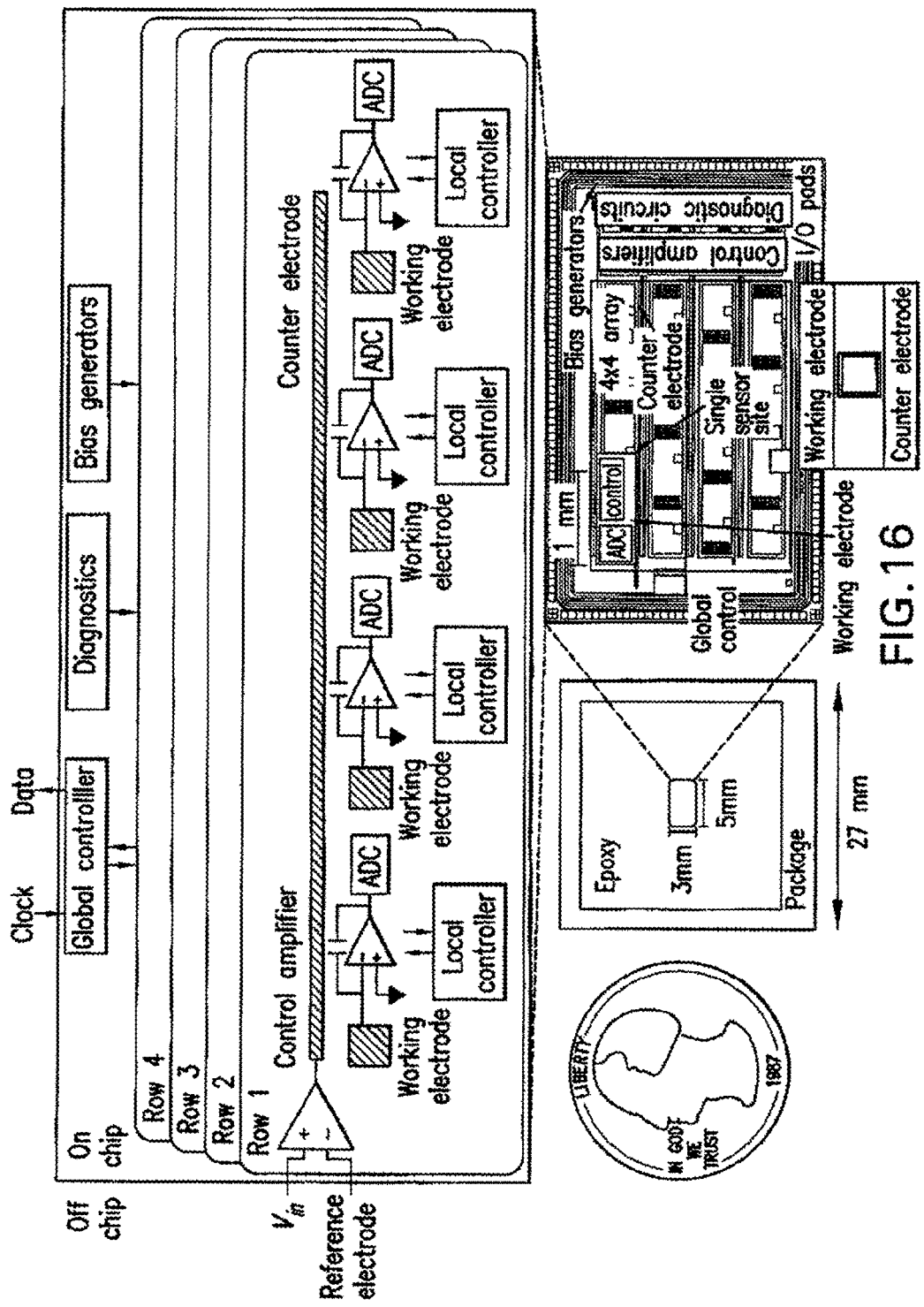
FIG. 16 depicts components according to an exemplary embodiment of the disclosed subject matter.

In other embodiments, "electrochemical impedance spectroscopy" (EIS) or single frequency "ac impedance" is used, in which the impedance of the electrode-electrolyte interface is determined by applying a small ac voltage signal to the cell and measuring the displacement current produced as shown in FIG. 15. If a range of input frequencies is used, a Nyquist plot of the impedance can be made. Fitting this data to a circuit model of the interface (as shown in the figure) provides information about the "double-layer" capacitance $C_{dl}$ in this region. This capacitance is known to change as a function of surface charge at the WE.

Figure 4:
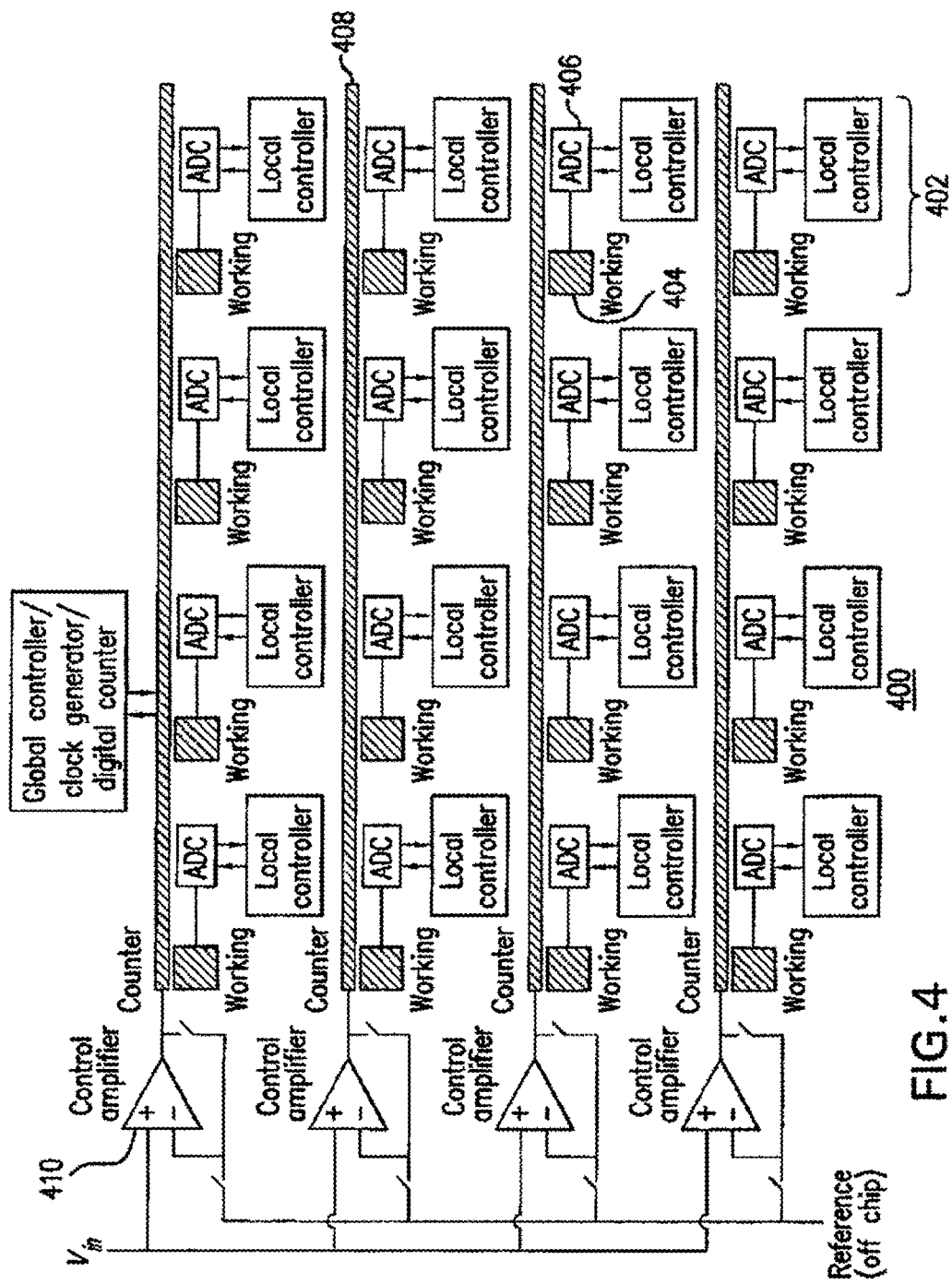
FIG. 4 depicts an architecture of the CMOS sensor array according to an exemplary embodiment of the disclosed subject matter.
Figure 5:
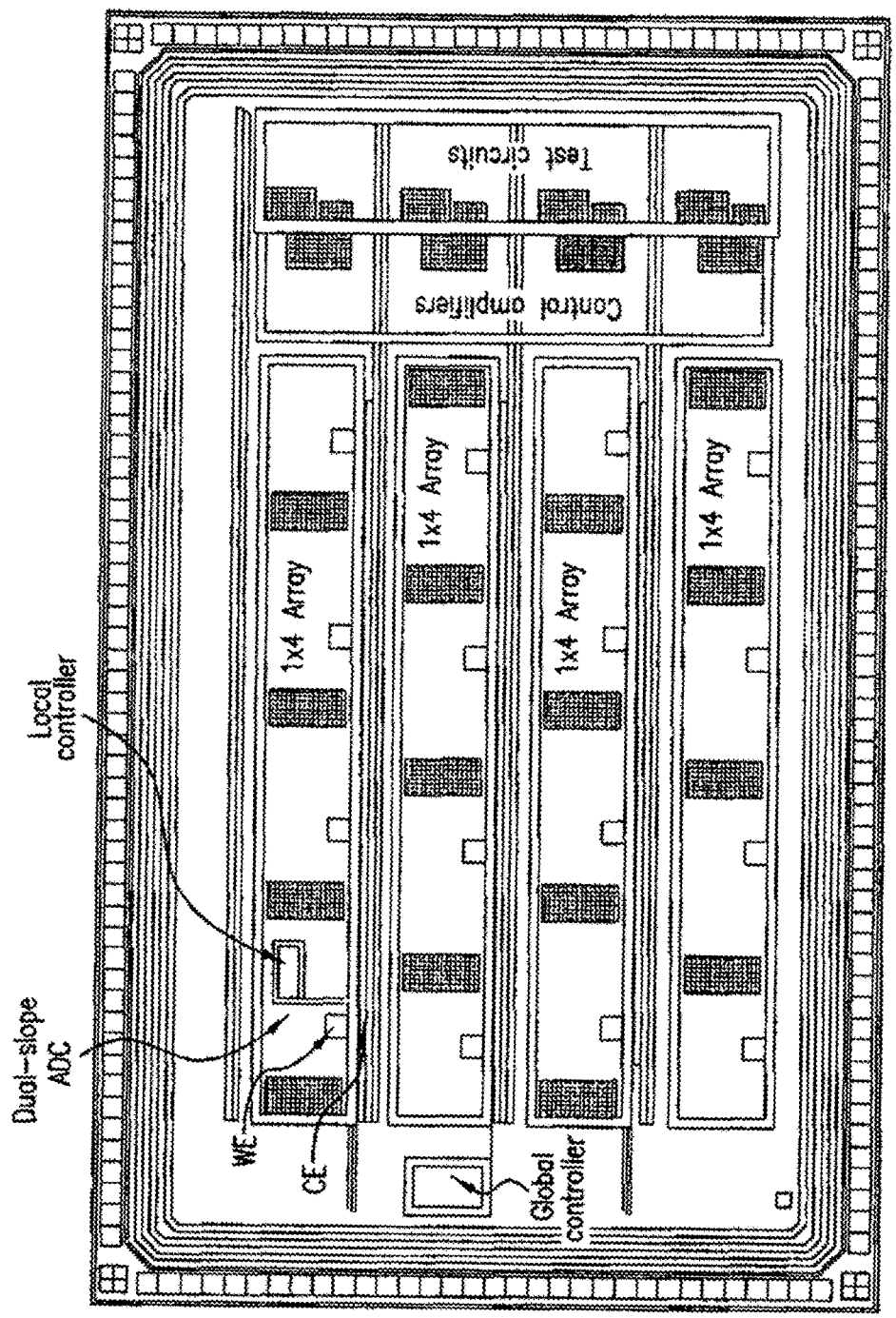
FIG. 5 depicts a die photograph according to the embodiment of FIG. 4.

In some embodiments, an active CMOS sensor array is employed for DNA sensing. One embodiment of an architecture of the active CMOS sensor array is shown in FIG. 4 and the accompanying die photograph is shown in FIG. 5. The chip can be fabricated in any conventional process, including but not limited to a 2.5-V, 5-metal, 0.25-μm CMOS process, measuring 5 mm-by-3 mm. Alternatively, a bipolar, BiCMOS, or SOI process can be used. Each array site 402 includes a square Au WE 404 and a dual-slope ADC 406 with digital control circuitry to digitize the current flowing through the electrode. The WEs in the top row have a side length of 100 μm with subsequent rows having lengths of 90, 80, and 70 μm. Such a variation permits demonstration of the effect of electrode area on the cell current for different redox and biomolecular reactions. It should be noted that any appropriate row lengths can be used, including equal row lengths. Each row of four WEs shares a 15-μm-by-2500-μm CE 408 driven by a control amplifier 410.

Figure 6:
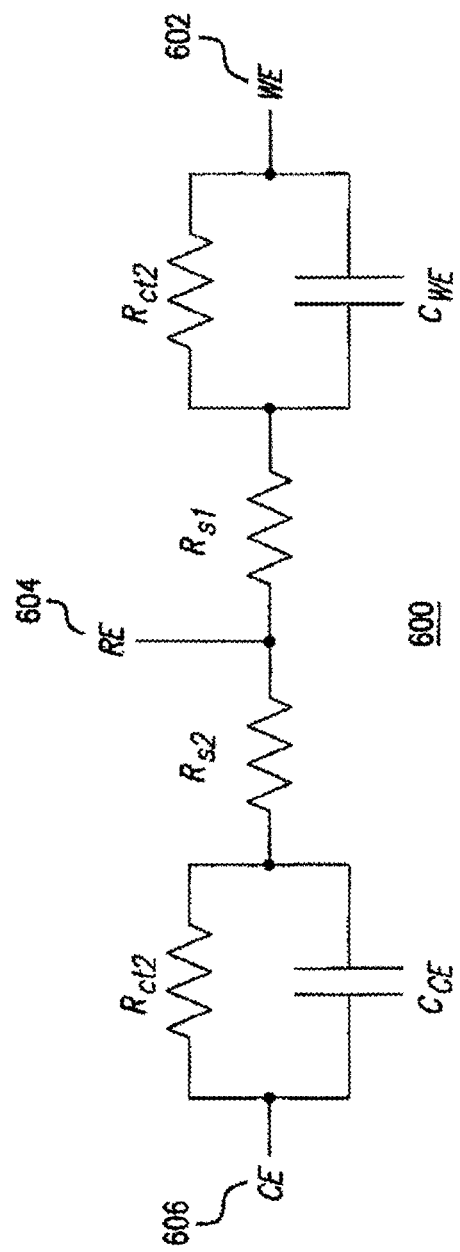
FIG. 6 depicts a circuit model according to another embodiment of the disclosed subject matter.

One embodiment includes the small-signal circuit model of the electrode-electrolyte interfaces in an electrochemical cell 600, shown in FIG. 6. In this example, resistors $R_{s1}$, and $R_{s2}$ represent the solution resistance between the WE 602 and RE 604, and CE 606 and RE 604, respectively. Based on impedance measurements of the electrochemical cell using a commercial potentiostat (e.g., a CHI 700C-series, available from CH Instruments, Austin, Tex.,) with a 125-μm-diameter Au WE (e.g., available from ESA Biosciences, Chelmsford, Mass., USA), platinum-wire (Pt-wire) CE (e.g., available from Sigma-Aldrich, St. Louis, Mo., USA), and a standard silver/silver-chloride/3-M sodium-chloride (Ag/AgCl/3-M NaCl) RE (e.g., available from Bioanalytical Systems, West Lafayette, Ind., USA), $R_{s1}$ ranges from approximately 275Ω in 1-M potassium phosphate buffer (PPB, pH 7.4) to 10 kΩ in 10-mM PPB. Capacitors $C_{WE}$, and $C_{CE}$ model the interfacial "double-layer" capacitance at the WE and CE, respectively. The measured value of $C_{WE}$ is on the order of 1 to 100 μF cm$^{-2}$, depending on the electrolyte composition and modification of the WE surface. Resistors $R_{ct1}$ and $R_{ct2}$ model the charge-transfer resistance at each surface, with the former having a typical measured value between 100 kΩ and 1 MΩ. The use of a three-electrode potentiostat configuration makes the measurement of the WE interface independent of the RE and CE impedances. However, knowledge of the $R_{ct1}$, $R_{ct2}$ and $C_{CE}$ values is used to test amplifier stability when designing the active sensor array.

The potentiostat circuits can provide good noise performance and stability across a wide range of operating conditions. The control amplifier (410 of FIG. 4) can be implemented with a two-stage, single-ended-output op amp having a dc gain of 87 dB. In one embodiment, when CV is carried out using low-frequency input signals, the amplifier can include input CMOS devices having a width and length of 4 mm and 1 μm, respectively, to reduce the effect of flicker (1/f) noise on the output. In addition, these large input-stage transistors can improve matching.

Figure 7A:
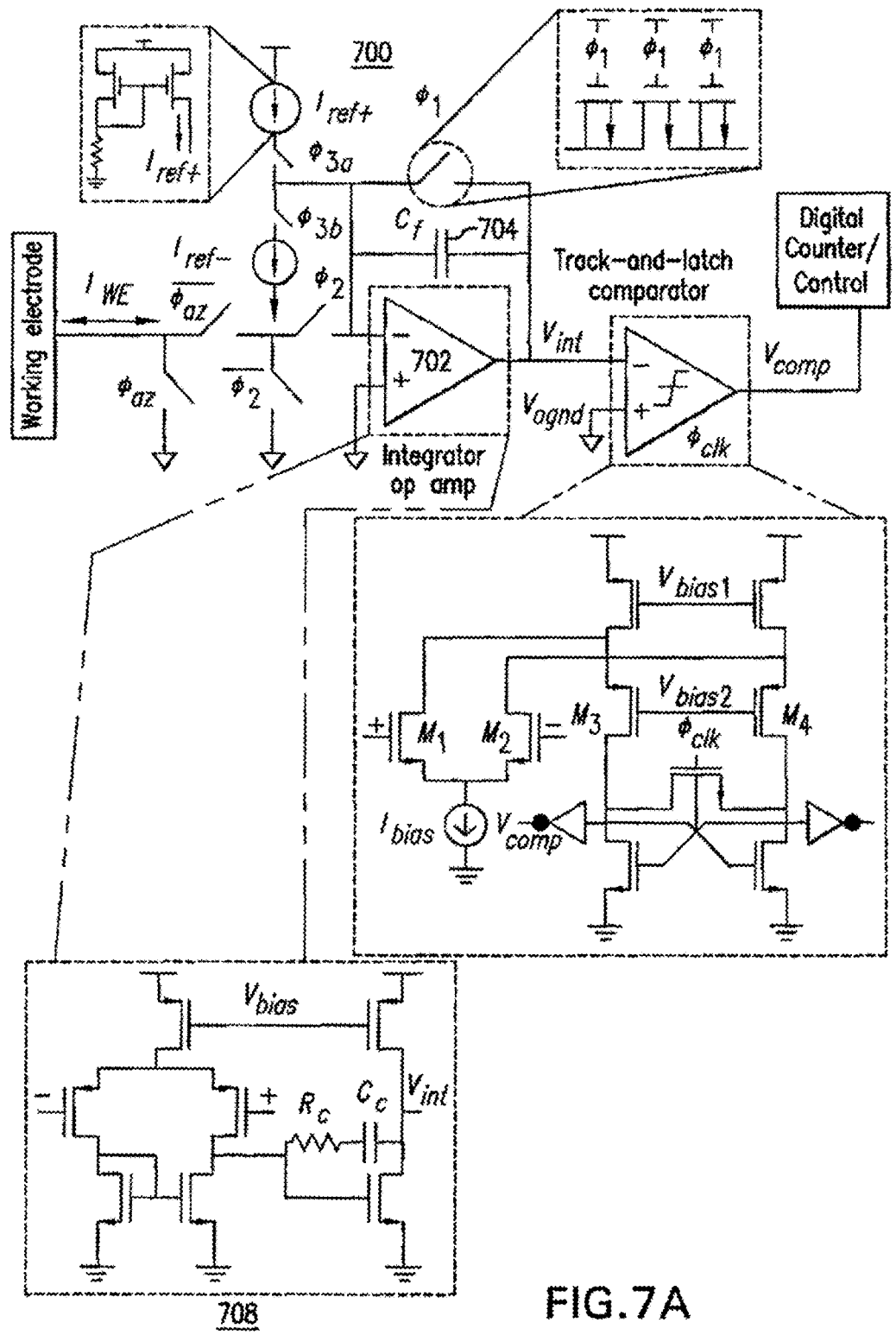
FIG. 7a depicts the architecture of a dual-slope ADC according to an exemplary embodiment of the disclosed subject matter.
Figure 7B:
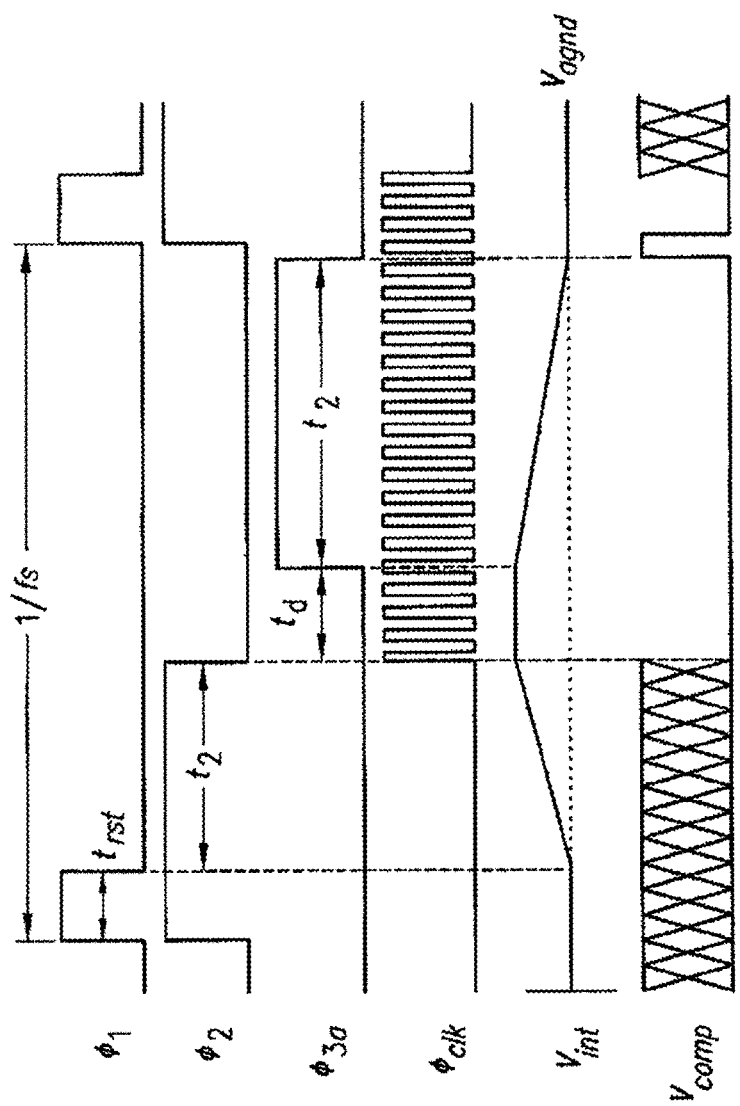
FIG. 7b depicts input and output voltage signals according to an exemplary embodiment of the disclosed subject matter.

Based on electrochemical measurements of redox species and DNA probe-target hybridization implementations using a commercial potentiostat and a 125-μm-diameter WE, it is determined that the integrated ADCs of the current embodiment can digitize currents in the 100-pA to 250-nA range that flow bidirectionally through the WE. In addition, since the maximum effective frequency of the input voltage stimulus used in the implementation is about 100 Hz, ADC operation at sampling rates up to 10 kHz can be sufficient to accurately reconstruct the cell current. In one embodiment, an example dual-slope ADC architecture, shown in FIG. 7*a*, can be used for this purpose because its dynamic range and sampling frequency can be adjusted. The ADC 700 includes of an integrating amplifier 702 with a fixed on-chip 5-pF linear capacitor 704, and track-and-latch comparator 706. NMOS switches are accompanied by "dummy" transistors to absorb injected charge during switching and digital counter with control logic. FIG. 7*b* shows the control signals, clocks, and integrator and comparator outputs for a typical ADC conversion cycle. After the integrator is reset during $t_{rst}$, current $I_{WE}$ is integrated onto capacitor $C_f$ for a fixed time interval $t_1$. During this period, the comparator clock $\phi_{dk}$, which operates at a higher rate than the ADC sampling frequency $f_s$, is gated in order to reduce the effect of switching interference on the integrator output. After $t_1$, $\phi_{dk}$ is enabled and the integrator output voltage $V_{int}$ is measured by the comparator during the period $t_d$. Based on the comparator output $V_{agnd}$, the capacitor is discharged using the appropriate constant current source $I_{ref+}$ or $I_{ref-}$ (for example, implemented using a PMOS and NMOS current mirror, respectively, biased with off-chip resistors) until $V_{int}$ crosses the comparator threshold (set to analog ground voltage $V_{agnd}$), signaling the end of the time period $t_2$. A counter, operated on $\phi_{dk}$, digitizes the time intervals and sets the nominal ADC resolution. The value of $I_{WE}$ can then be calculated from $(t_2/t_1)I_{ref}$. Auto-zeroing, in which the integrator offset is sampled prior to digitizing the cell current, can be performed by setting the $\phi_{az}$ signal appropriately. This procedure implements offset correction in addition to mitigating the effect of 1/f noise on the output.

The integrator op amp 708 can have the same or similar architecture as the control amplifier, with similar input transistor sizes to reduce 1/f noise. To maintain closed-loop stability, op amp 708 is compensated with a 25-pF metal-insulator-metal (MIM) capacitor $C_c$ in series with a 150-Ω polysilicon resistor $R_c$ between the first and second stages. In some embodiments, based on computational analyses of the electrochemical interface circuit model, in which the component values are varied around their measured values, a minimum phase margin of 45° is obtained. This technique also takes into account component process, voltage, and temperature (PVT) variation as well as the effect of the input impedances of other WEs and ADCs in the array during parallel operation. In addition, extensive computational transient analyses are carried out to ensure stability when large-signal inputs are applied to the electrochemical cell, as required in CV.

In some embodiments, the total bias current required by the integrator op amp 708 can be, for example, 4 mA. With this bias, a temperature increase of 3.5° C. is observed when the chip is performing electrochemical measurements with all ADCs running simultaneously. No deleterious effects occur during biomolecular detection experiments due to this temperature increase.

The track-and-latch comparator following the integrator can make correct decisions with a clock frequency up to, for example, at least 50 MHz. Transistors $M_3$ and $M_4$ separate the cross-coupled switching transistors at the output from the drains of input transistors $M_1$ and $M_2$ to reduce kickback interference. In one embodiment, the latter transistors have a width and length of 200 μm and 1 μm, respectively, to reduce offset due to mismatch.

Integrated transconductance amplifiers can be included to test the operation of the ADCs. Each amplifier contains an op amp driving the gate of a large NMOS or PMOS transistor (depending on the desired current direction) with its inverting input connected to an off-chip 10-MΩ resistor that is connected to either the supply voltage or ground. The feedback loop ensures that the applied voltage at the non-inverting input is established across the resistor. Currents up to 150 nA can then he forced into the ADC using full-rail input voltages.

In some embodiments, post-processing of the fabricated chip can be performed to create an array of electrodes on the surface of the chip. In one embodiment, the electrodes can be formed using Au, but other suitable, conducting materials can be used, including platinum, indium-tin-oxide, highly doped silicon, conducting carbon paste and conducting polymers, silver, silicon dioxide, graphite, etc. Au can be relatively electrochemically inactive in the presence of strong electrolytes and is easily modified by self-assembly of well-ordered monolayers of thiol, sulfide, or disulfide compounds through Au-sulfur bonding. As a result, thiolated ssDNA probes can be strongly bound to Au surfaces.

Figure 8A:
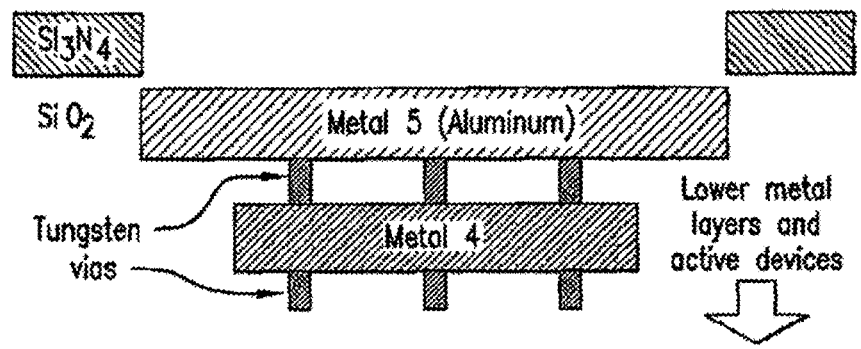
FIG. 8a depicts a cross section of CMOS die before post-processing according to an exemplary embodiment of the disclosed subject matter.
Figure 8B:
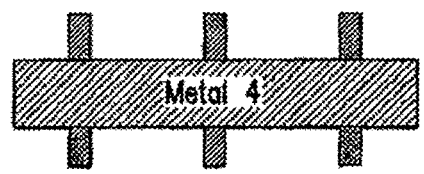
FIG. 8b depicts a result of a wet etch process according to an exemplary embodiment of the disclosed subject matter.
Figure 8C:
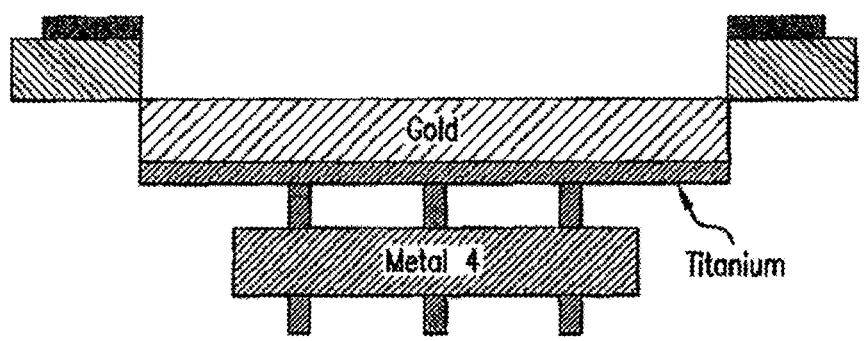
FIG. 8c depicts an electrode according to an exemplary embodiment of the disclosed subject matter.

FIGS. 8*a-c* demonstrate CMOS post-processing procedures applicable to some embodiments for fabricating a surface electrode array. FIG. 8*a* shows a cross section of a CMOS die before post-processing showing the top two aluminum (Al) metal layers at one electrode site. FIG. 8*b* shows the result of a wet etch process to remove the top Al metal layer. FIG. 8*c* shows the final electrode resulting from Ti—Au thin-film deposition.

In some embodiments, CMOS technologies use stacked metal layers connected vertically by tungsten (W) "vias" to route electrical signals and form transistor interconnects and can be passivated with $SiO_2$ and $Si_3N_4$ at the chip surface. In some embodiments, at the time of layout, openings in the chip passivation layers are defined at the desired electrode sites above the top-metal aluminum layer in a manner similar to that for making bond pads or probe pads, as shown in FIG. 8*a*. In some embodiments the openings can be square openings while in alternative embodiments, other shaped openings can be used as appropriate, such as circular, rectangular, hexagonal, etc. Any suitable technique can be used for forming the openings, such as inductively-coupled plasma (ICP) etching. Al is an electrochemically active metal that can, in some instances, become corroded and in some applications can be replaced as necessary. In some embodiments, after chip fabrication, the WEs are post-processed by first selectively removing the exposed Al metal at the electrode sites using, for example, a wet-etch process as displayed in FIG. 8b. One example of such a process is a phosphoric-acid wet etch technique. Other suitable techniques for removing the Al metal include sodium hydroxide wet etching or ICP etching. This is followed by the electron-beam deposition of 20 nm of an adhesion layer, for example, Ti. Any adhesion layer at any appropriate thickness can be added, including Cr. In some embodiments, one or more additional layers can be added on top of the adhesion layer, such as an Au layer as already described. In one example embodiment, a 300-nm layer of Au is added, followed by a lift-off process to form the final electrodes in FIG. 8c. It should be noted that any appropriate material and thickness of the material can be used to form the electrodes, such as 200 nm of Au. These electrodes can connect directly to the tungsten (W) vias of the CMOS back end. The foregoing techniques of electrode fabrication require fewer lithographic steps than the construction of a "stepped" electrode structure and do not require the implementation of a full CMOS back-end process. Such a procedure results in lower fabrication costs and complexity because it is more easily implemented in existing CMOS technologies. In some embodiments, the CEs are fabricated in a similar way as the WEs.

In one example embodiment, the post-processed chip can be set in a 272-pin, 27 mm-by-27 mm, ball-grid array (BGA) package with the die surface exposed. The metal bond wires connecting the input-output (I/O) pads along the chip perimeter can be shielded from electrolyte exposure through encapsulation in a heat-cured, chemical resistant epoxy such as Hysol FP4450HF and FP4451TD (available from Henkel, Dusseldorf, Germany) or EPO-TEK GE116 and GE120 (available from Epoxy Technology, Billerica, Mass., USA). The packaged chip can be fastened in a surface-mounted printed-circuit board (PCB) socket with a top-plate. A 1-mm thick polydimethylsiloxane (PDMS) sheet, having a square opening in the center to expose the chip surface, can be introduced between the chip and top-plate to prevent electrolyte leakage onto the PCB. A 10-mL glass reservoir, attached to the top-plate using epoxy, can hold the liquid analyte in contact with the chip surface. An external Ag/AgCl/3-M NaCl reference electrode can be held in the reservoir with a Teflon cap.

Electrical characterization of the active CMOS sensor array, along with results from electrochemical demonstrations involving redox species and DNA detection are illustrated in an example embodiment.

Figure 9:
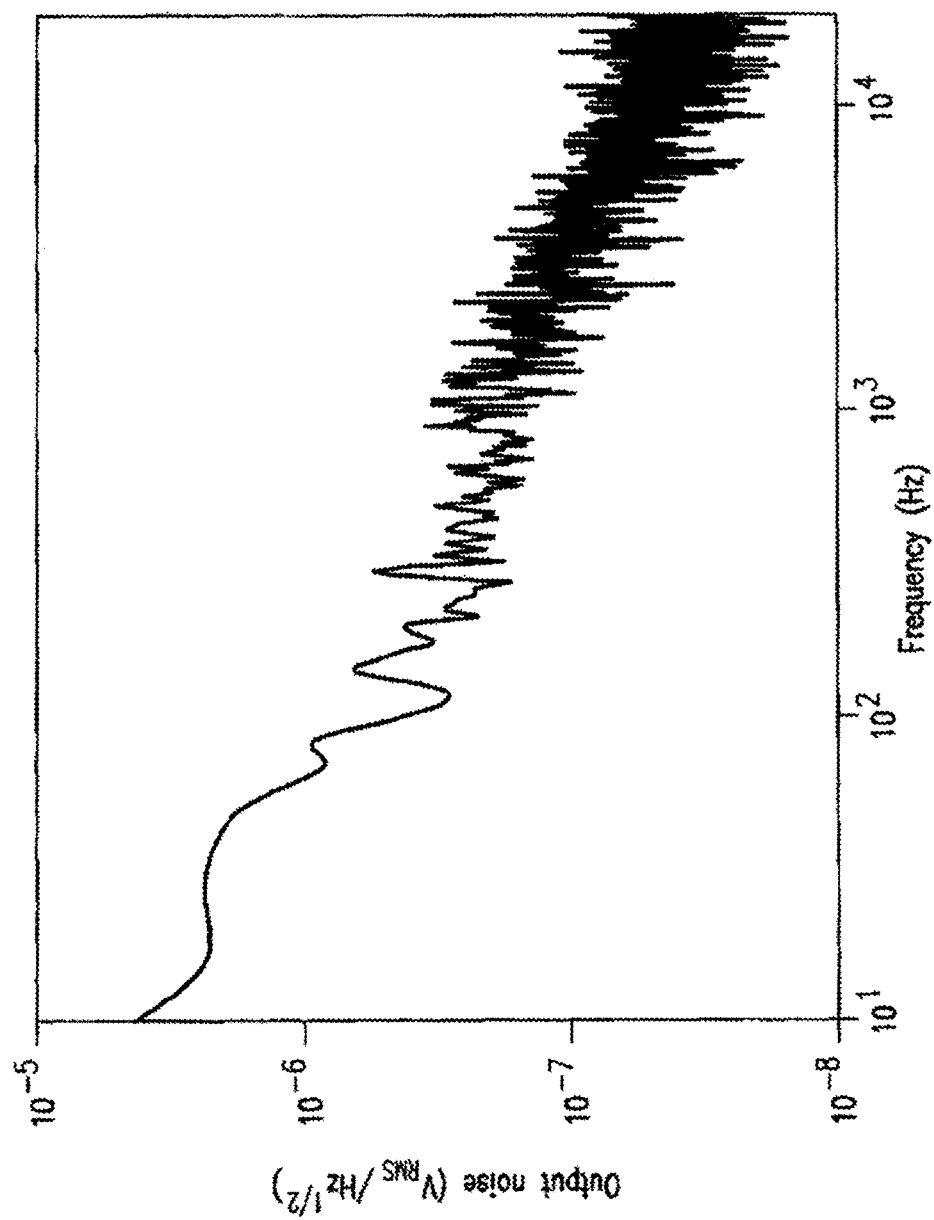
FIG. 9 depicts an output noise spectrum according to an exemplary embodiment of the disclosed subject matter.

FIG. 9 shows the output noise spectrum of the control amplifier of some embodiments over a bandwidth from 10 Hz to 21 kHz when the device is operated in a unity-gain configuration. The corner frequency is located around 10 kHz. The measured output noise voltage is 21.2 $\mu V_{rms}$ over the 10-Hz to 21-kHz band when the effect of 60-Hz line interfering tones and other interfering tones are neglected.

In some embodiments, characterization of the dual-slope ADC at each sensor site is carried out using the on-chip test circuits. To allow sufficient bandwidth for CV demonstrations, the ADCs are operated at an $f_s$ of 2.5 kHz with $\phi_{clk}$ set to 3.5 MHz. Integration time $t_1$ is set to 23 µs and discharge time $t_2$ is allowed a maximum value of 315 µs, providing a nominal resolution of 10 bits. The remaining time during each conversion cycle is required to reset $C_f$ and select the appropriate reference current source. The maximum $I_{in}$ before integrator saturation using these settings is about 110 nA. Reference currents $I_{ref+}$ and $I_{ref-}$ are set to 15 nA and 18 nA, respectively. DNL and INL values for the ADCs can be −0.25 LSB and +0.38 LSB, respectively, with an LSB current of approximately 240 pA.

Figure 10A:
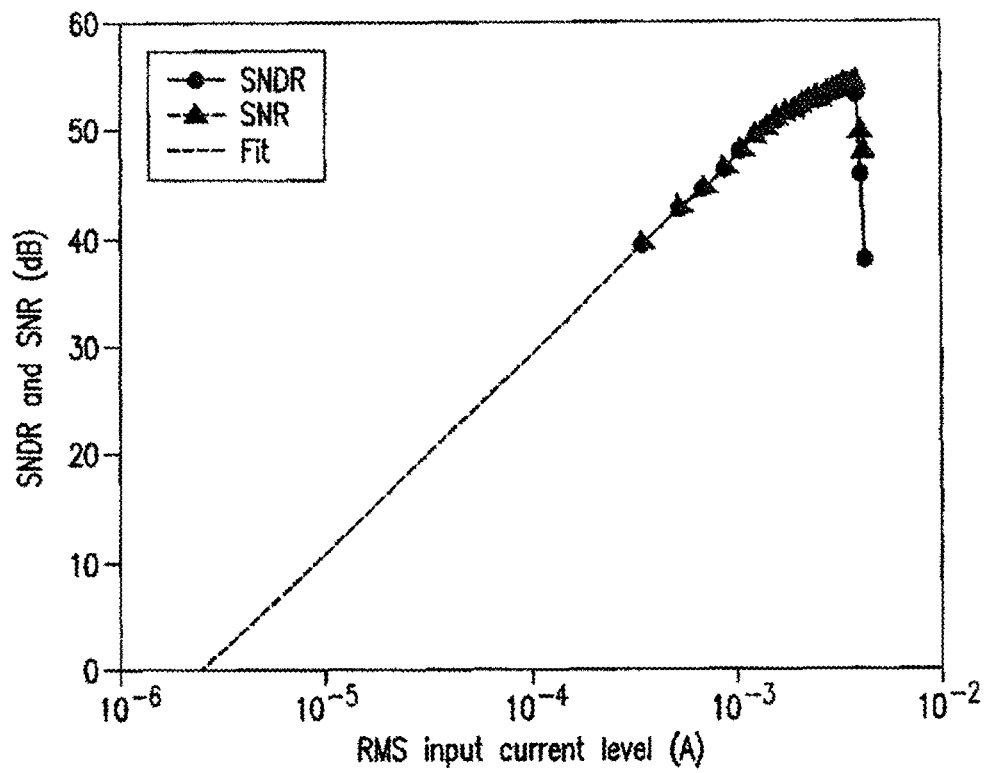
FIGS. 10a and 10b depict test results for an ADC according to an exemplary embodiment of the disclosed subject matter.
Figure 10B:
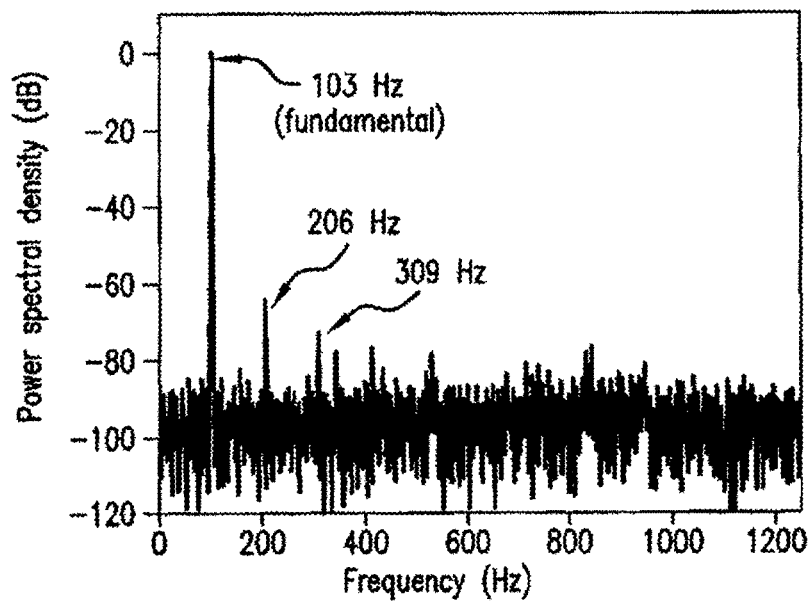

Dynamic range (DR) of the ADC is verified using a 103-Hz sinusoidal input current. FIGS. 10a-b demonstrate measured results from example ac linearity testing of the dual-slope ADC: (a) shows dynamic range and (b) shows output spectrum with a full-scale input at 103 Hz (resolution bandwidth is 0.31 Hz). FIG. 10a displays the signal-to-noise ratio (SNR) and signal-to-noise-and-distortion ratio (SNDR) of the ADC as a function of input current level. The lower end of the DR curve is fitted due to the inability to provide a sufficiently small ac voltage signal to the on-chip transconductance amplifiers for ADC testing. The DR is limited at the high end by integrator saturation. A maximum effective resolution (ENOB) of 9 bits is achieved and is limited by the linearity of the test circuits. A DR of greater than 10 bits is achieved from computational circuit analyses of the dual-slope ADC alone. FIG. 10b shows the result of an 8192-point fast Fourier transform (FFT) of the measured ADC output when a full-scale input is applied. The strong second harmonic is due to the single-ended architecture of the ADC.

The redox species potassium ferricyanide, $K_3[Fe(CN)_6]$, is an exemplary compound used by electrochemists to study interfacial properties due to its highly-reversible behavior. At the appropriate potential, ferricyanide ions are reduced to ferrocyanide ions in the reaction $Fe(CN)_6^{3-}+e\rightarrow Fe(CN)_6^{4-}$. In some embodiments, the use of the active CMOS sensor array for electrochemical sensing, CV measurements of 2-mM potassium ferricyanide in 1-M PPB (pH 7.4) are carried out. In these illustrations, the potential between the WEs in the array and the RE is scanned from +0.75 V to −0.5 V and back at various rates while the cell current is observed at one WE. Prior to running the electrochemical experiments, organic contaminants on the chip surface are removed by placing the packaged chip in an ultraviolet (UV)/ozone cleaning device (e.g., the T10×10/OES, available from UVOCS, Montgomeryville, Pa., USA) for 5 min followed by thorough rinsing in deionized water (e.g., 18.2 MΩ cm).

Figure 11A:
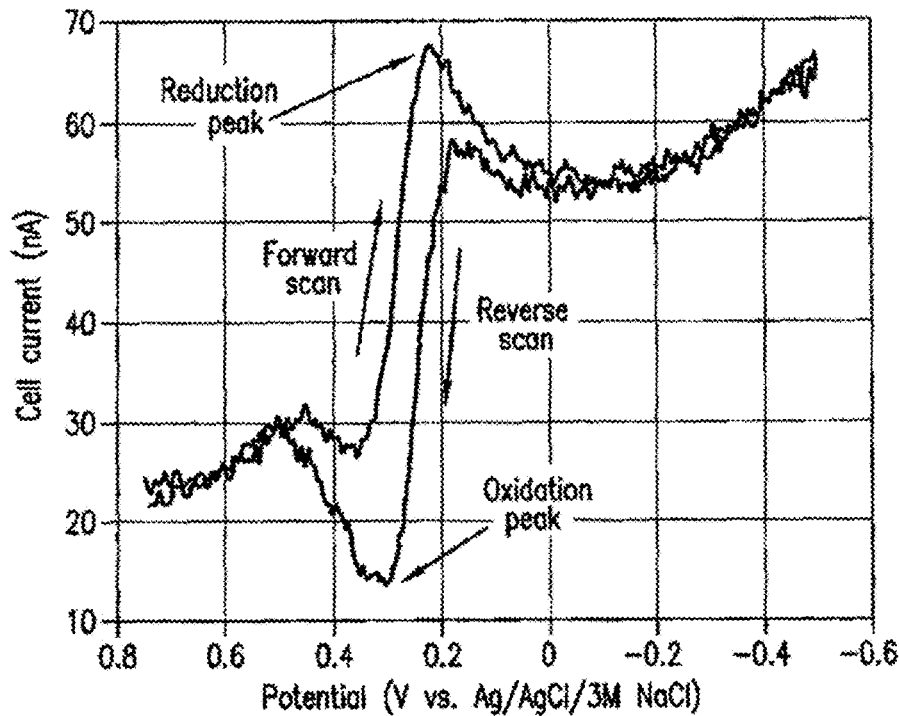
FIGS. 11a and 11b depict measured cell currents from an electrochemical redox reaction according to some embodiments of the disclosed subject matter.

FIG. 11a shows the cell current at one of the 100-µm WEs when an input scan rate of 72 mV/s used. A zero-phase, low-pass FIR filter is used to post-process the raw data in MATLAB. The location of the forward (reduction) and reverse (oxidation) current peaks at +0.22 V and +0.30 V, respectively, match those obtained when the same experiment is run on a commercial potentiostat using a 125-µm-diameter Au WE. In addition, this 80-mV difference in peak potentials is relatively close to the theoretical value of 59 mV for a fully-reversible, single-electron redox process 120. The magnitude of the current falls after each peak due to mass-transport limitations of the redox species to the WE surface.

Figure 11B:
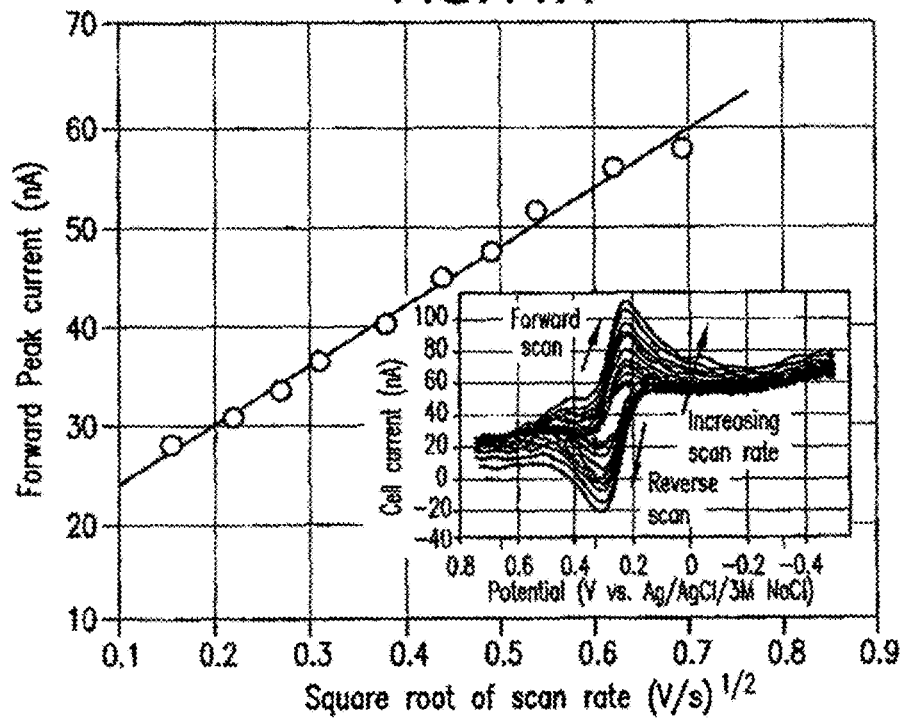

In FIG. 11b, v is increased from 24 mV/s to 480 mV/s and the peak reduction current is measured. It has been shown that the peak current $i_p$ at a planar electrode for a reversible reaction under diffusive control exhibits the relationship $i_p \propto AD_O^{1/2}C_O^*v^{1/2}$, where A is the WE area, and $D_O$ and $C_O$ are the diffusion coefficient and bulk concentration of the oxidized species, respectively. Therefore, $i_p$ (measured from the charging current background) increases linearly with $v^{1/2}$, as is observed in FIG. 11b.

Figure 12:
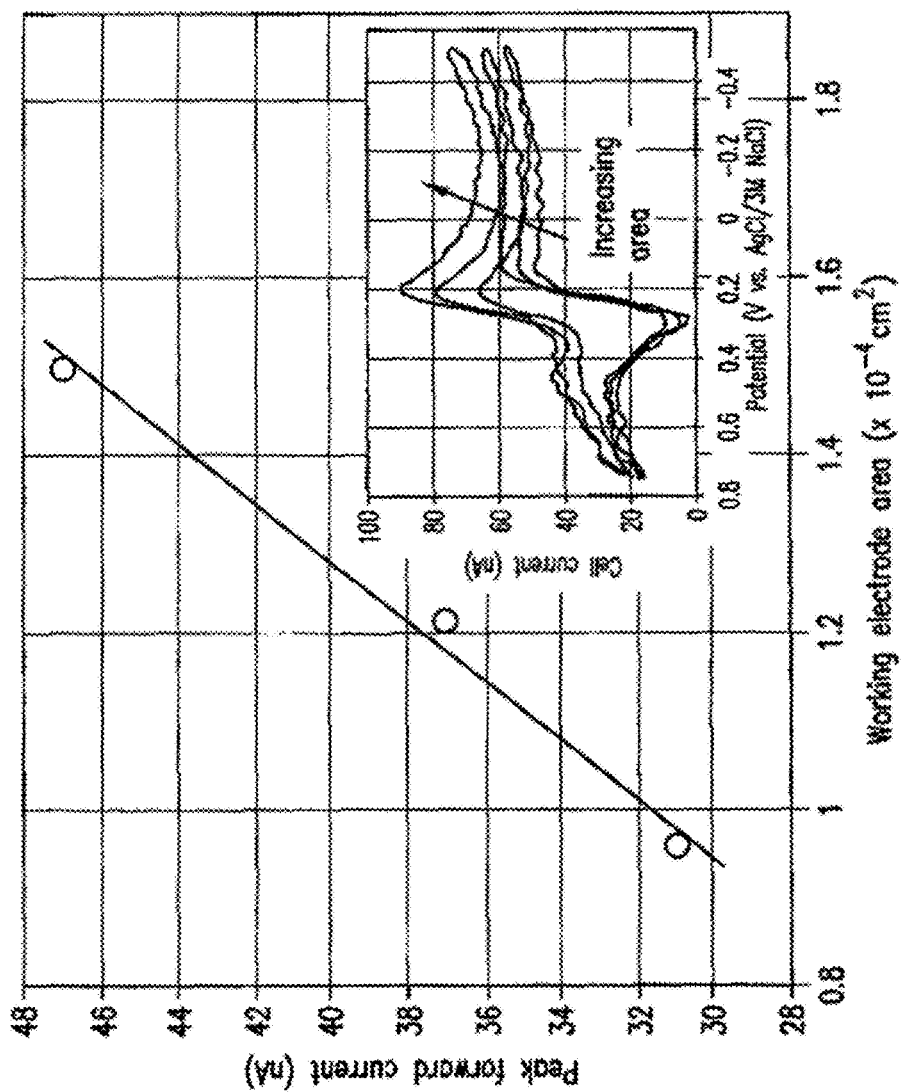
FIG. 12 depicts measured results according to an exemplary embodiment of the disclosed subject matter.

The linear dependence of $i_p$ on WE area is also verified by running a CV scan at 290 mV/s and observing the current flowing through the 100-, 90-, and 80-μm WEs. FIG. 12 shows the results from this measurement. Surface roughness of the electron-beam-deposited Au layer causes the actual electrode area to be larger than its geometric (drawn) area by a factor of about 1.5. This has been accounted for in the results.

In one example embodiment, to demonstrate the use of the active CMOS array for biomolecular detection, the Au WEs are functionalized with a monolayer of ssDNA probes. CV measurements are then carried out in the presence of the redox species hexaamineruthenium (III) chloride (RuHex$^{3+}$) to determine probe surface density. The redox-active counterion RuHex$^{3+}$ associates with the surface-immobilized DNA, causing the thermodynamics of the redox processes to be altered as a result. It is known that as probe coverage increases, the reduction potential for the reaction RuHex$^{3+}$+e→RuHex$^{2+}$ shifts toward more negative values due, in part, to changes in local charge concentration, dielectric constant, spatial distribution, and solvation. Once calibrated, these measurements can be used to determine the probe surface coverage.

In some embodiments, the chip is cleaned as described previously and incubated for 30 min in a 1-M MgCl$_2$ solution containing a known concentration of thiolated 20-mer DNA probe. Next, the chip is incubated in 1-mM mercaptopropanol (MCP) solution (e.g., available from Aldrich, St. Louis, Mo., USA) for 90 min, forming a self-assembled monolayer which helps to passivate partially the WE surface and prevent nonspecific interactions between the DNA and WE. CV at a scan rate of 4 V/s is then carried out in 7 mL of 10-mM Tris buffer (pH 7.4) with 1-μM RuHex$^{3+}$.

Figure 13:
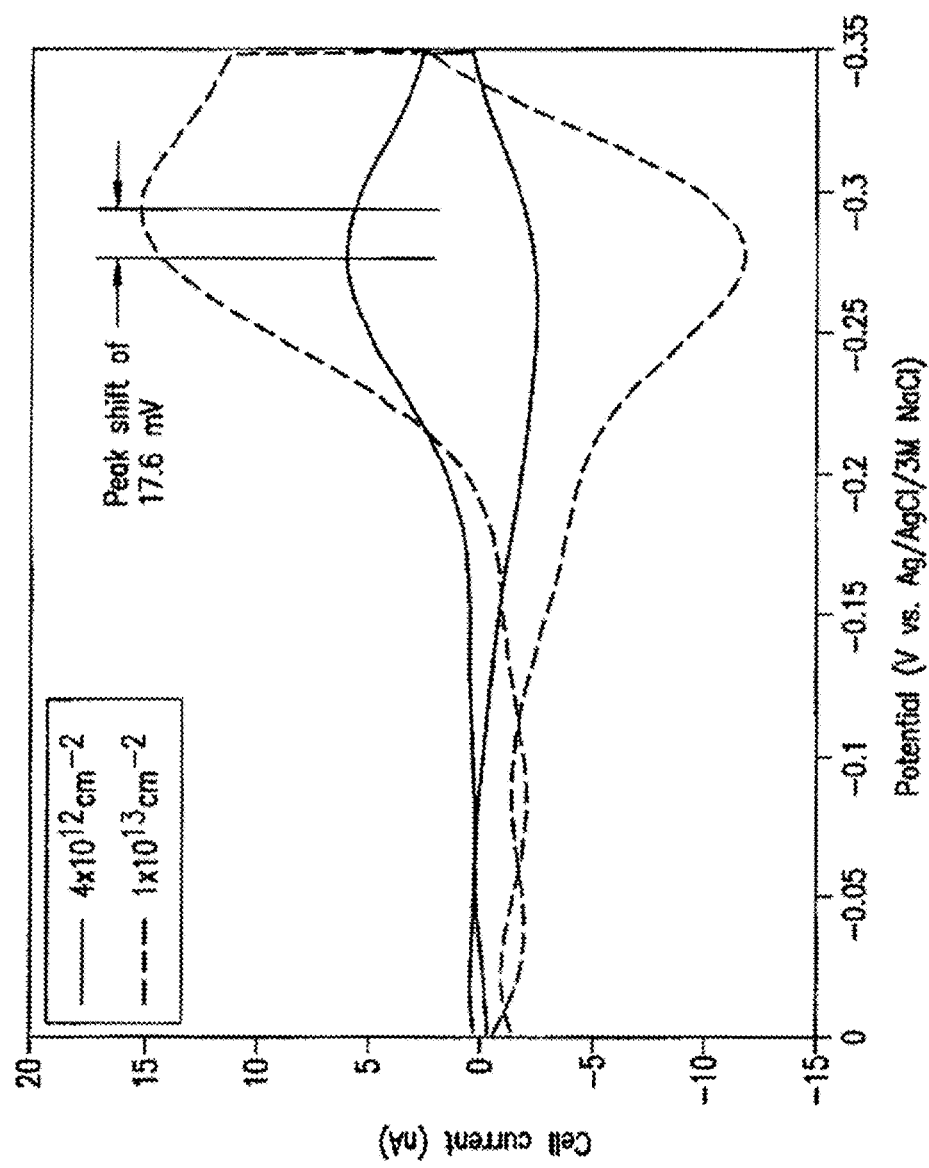
FIG. 13 depicts results according to another embodiment of the disclosed subject matter.

FIG. 13 shows the results from two different CV demonstrations at one 90-μm WE for DNA probe coverages of $1\times10^{13}$ cm$^{-2}$ and $4\times10^{12}$ cm$^{-2}$. These probe densities are obtained by incubating the chip in different concentrations of DNA probe solution and are verified using a set of calibration measurements on a commercial potentiostat with 125-μm-diameter Au WE. The overall shape of the CV curves is different than those obtained in the foregoing section because, in this case, RuHex$^{3+}$ is a surface-adsorbed species which is not subject to mass-transport limitations.

The forward peaks occur at −277.2 mV and −294.8 mV for the lower and higher probe coverages, respectively. This indicates a shift of 17.6 mV toward more negative potentials with the higher coverage, confirming previous observations. Parallel experiments on a commercial potentiostat show similar peak potentials and a closely-matching shift of 15.4 mV. In addition, the quantity of RuHex$^{3+}$ near the WE increases with higher probe coverages, as is evident in the observed peak-current increase for the $1\times10^{13}$ cm$^{-2}$ curve.

In another example embodiment, quantitative, real-time, electrochemical detection of DNA probe-target hybridization is carried out using the active CMOS sensor array. Single-stranded DNA target molecules are each covalently modified (conjugated) with one or more N-(2-ferrocene-ethyl) maleimide redox labels [referred to simply as "ferrocene" (Fc)] that undergoes the reaction Fc→Fc$^+$+e over a well-defined potential range. Fc redox labels are known to be chemically stable and are electrochemically reversible. They are one example alternative to the use of radioactive isotopes for nucleic-acid sequencing and sensing. Fc redox labels have been used to study the thermodynamics of DNA probe binding and to perform label-based detection of RNA hybridization, among various other applications. When labeled targets are introduced into an environment containing surface-bound probes, the number of target molecules that hybridize can be determined, in some instances, by an equilibrium that depends on such factors as the relative probe and target concentrations, buffer ionic strength, and temperature. Upon hybridization, the amount of bound target is measured from the charge transferred due to the Fc reaction, with one electron contributed by surface-bound target on the WE. This value can be determined, for example, from CV measurements by integrating the area enclosed by the Fc redox current after subtraction of background charging contributions, and then dividing the result (in Coulombs) by the magnitude of the electronic charge ($1.602176\times10^{-19}$ C) and electrode area. This technique differs from "intercalation"-based approaches to DNA detection because the latter approach cannot provide a measure of the absolute amount of probe-target hybridization on the WE surface. In addition, alternative "sandwich"-based assays cannot provide a quantitative measure of target coverage in real time because the redox-active molecules are added after hybridization has occurred.

In one embodiment, the sequences of the 3'-end thiolated 20-mer DNA oligonucleotide probes (e.g., available from MWG-Biotech, High Point, N.C., USA) used in the CMOS biosensor array experiments are as follows: P1 5'-TTT TAA ATT CTG CAA GTG ATJ-3' (from *Homo sapiens* retinoblastoma 1 mRNA) and P2 5'-TTT TTT TCC TTC CTT TTT TTJ-3'; where J represents a thiol group. The target sequences (e.g., also available from MWG-Biotech) are as follows: T1 5'-FcCAC TTG CAG AAT TTA AAA-3' and T2 5'FcAAA AAG GAA GGA AAA AAA-3'. Sequences P1 and T1, and P2 and T2, are pairwise complementary, respectively, do not exhibit self-complementarity, and will not cross-hybridize. These model sequences demonstrate the functionality of the active CMOS biosensor array platform and allow verification against results from off-chip electrochemical experiments using similar sequences.

Figure 21:
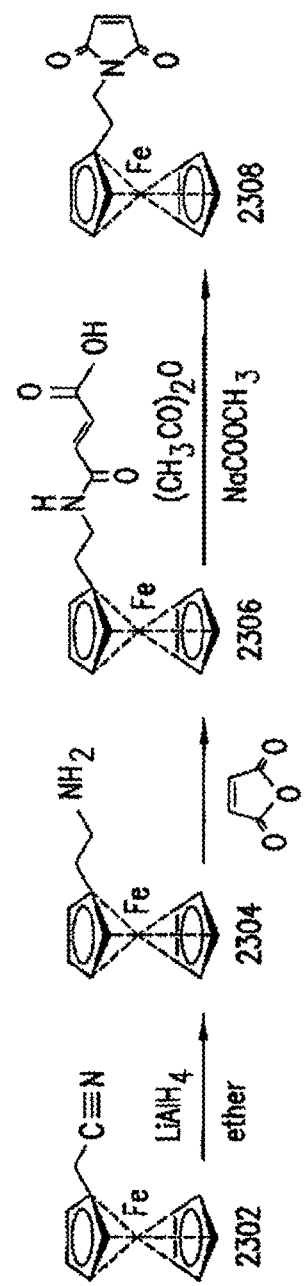
FIG. 21 depicts a procedure according to an exemplary embodiment of the disclosed subject matter.

FIG. 21 illustrates one embodiment for the synthetic protocol for preparation of the N-(2-ferrocene-ethyl) maleimide redox label 2308 starting from ferrocene acetonitrile 2302. In practice, any well known procedure can be employed. Chemicals used in this procedure are available from, for example, Aldrich, St. Louis, Mo., USA. N-ferrocene ethylamine 2304 is made by adding 100 mL dry ether to 0.68 g lithium aluminum hydride (LiAlH$_4$, 18 mmol) with argon protection, followed by mild stirring. The LiAlH$_4$/ether mixture is placed in an ice bath and 1 g (4.5 mmol) ferrocene acetonitrile 2302 solid is added slowly. The ice bath is then removed and the reaction is allowed to proceed for 2 h, after which the reaction mixture is slowly quenched with concentrated NaOH while on ice. The pH of the final aqueous phase is measured to confirm basicity and thus the completion of quenching. Next, MgSO$_4$ is added slowly to the mixture to remove water, and is subsequently removed by filtering. The remaining mixture is loaded on a silica gel column, washed with ether, followed by washing with ethyl acetate. The column is then eluted with the mixture ethyl acetate (75%)/methanol (20%)/triethylamine (5%). The entire elute is collected and concentrated under vacuum overnight to obtain 0.63 g dark-brown viscous liquid, with 60% yield.

N-ferrocene ethyl maleamic acid 2306 is made by dissolving 250 mg (1 mmol, MW=229) ferrocene ethylamine 2304 in 1.5 mL ice-cold dry tetrahydrofuran and mixing with 150 mg (1.5 mmol) maleic anhydride, also dissolved in ice-cold tetrahydrofuran. The mixture is allowed to react for 3 h with stirring at 4° C., followed by solvent evaporation. The crude reaction mixture is washed with ether twice, concentrated, and dried to obtain 280 mg of a yellow solid with 80% yield and a melting point of 128-130° C.

The final product is formed by adding 250 mg (0.75 mmol) of N-ferrocene ethyl maleamic acid 2306 to a solution of 2 mL acetic anhydride containing 15% sodium acetate. The resulting mixture is heated to 70° C. for 3 h with stirring. $H_2O$ and $NaHCO_3$ are added to the mixture to neutralize remaining acetic acid. The reaction mixture is then extracted with 10 mL ethyl acetate three times. The organic phases are collected and dried over $MgSO_4$. Next, the solution is concentrated, applied onto a silica gel column, and the product is eluted with ethyl acetate (15%)/hexane (85%). The pure fractions are pooled and the solvent evaporated off to give 63 mg yellow solids with a melting point of 98-100° C.

In some embodiments, the DNA target labeling procedure is as follows. Target oligonucleotides, thiolated at the 5' end by the manufacturer, are first deprotected with dithiothreitol (e.g., DTT, available from Aldrich, St. Louis, Mo., USA) to liberate the thiol group. They are then purified on a size-exclusion column (e.g., PD-10, available from Amersham Biosciences, Piscataway, N.J., USA), and reacted with Fc overnight in 150 mM potassium phosphate buffer (e.g., PPB, pH 8.0, available from Fisher, Pittsburgh, Pa., USA) at a nominal DNA concentration of 24 μM and a 50-fold excess of Fc. The resulting ferrocene-modified targets are purified on PD-10 and oligonucleotide purification cartridge (e.g., OPC, available from Applied Biosystems, Foster City, Calif., USA) prep columns, followed by reverse-phase HPLC purification on, for example, a Beckman Coulter system (available from Beckman Coulter, Fullerton, Calif., USA) including a Model 125 high-pressure gradient HPLC pump and a Model 168 multi-wavelength diode array detector and equipped with a C-18 reverse-phase analytical column. A flow rate of 0.5 mL $min^{-1}$ and a linear gradient of 12%-100% methanol in a solution containing 8.6 mM triethylammonium and 100 mM hexafluoroisopropyl alcohol in water (pH 8.1) are used. The desired product is collected and evaporated under vacuum until dry. In some embodiments, the incorporation of redox-labeled single nucleotides into DNA using standard polymerase chain reaction (PCR) techniques has been used, providing capability for the labeling of target molecules in complex DNA sample mixtures.

Detection of DNA probe-target hybridization with the active CMOS sensor array is carried out by scanning from zero to +0.35 V and back at v of 60 V/s. Due to the relatively high scan rate required, the sampling rate of the dual-slope ADCs is increased to 10 kHz with $\phi_{clk}$ set to 3.5 MHz. The fixed integration and maximum discharge times are 15 μs and 63 μs, respectively. At this setting, the typical measured SNDR is 43.7 dB at a current a level of 38 $nA_{rms}$ (corresponding to a level of −6 dBFS) and the maximum DNL and INL are +0.22 LSB and +0.15 LSB, respectively.

In some embodiments, the chip surface is cleaned as described previously. Next, a layer of ssDNA probes at each WE is constructed by incubating the surface of the chip in 1 M $MgCl_2$ solution containing 500 nM probe for 30 min. This provides a probe surface density of approximately $8\times10^{12}$ $cm^{-2}$, determined from a set of calibration measurements performed off chip. After probe immobilization, the chip is incubated in a 1 mM MCP solution for 90 min which forms a self-assembled monolayer on the Au WEs. The CV demonstrations are run in 7 mL of 1 M PPB (pH 7.4), for example, made by combining appropriate amounts of $K_2HPO_4$ and $KH_2PO_4$ in water.

Figure 17:
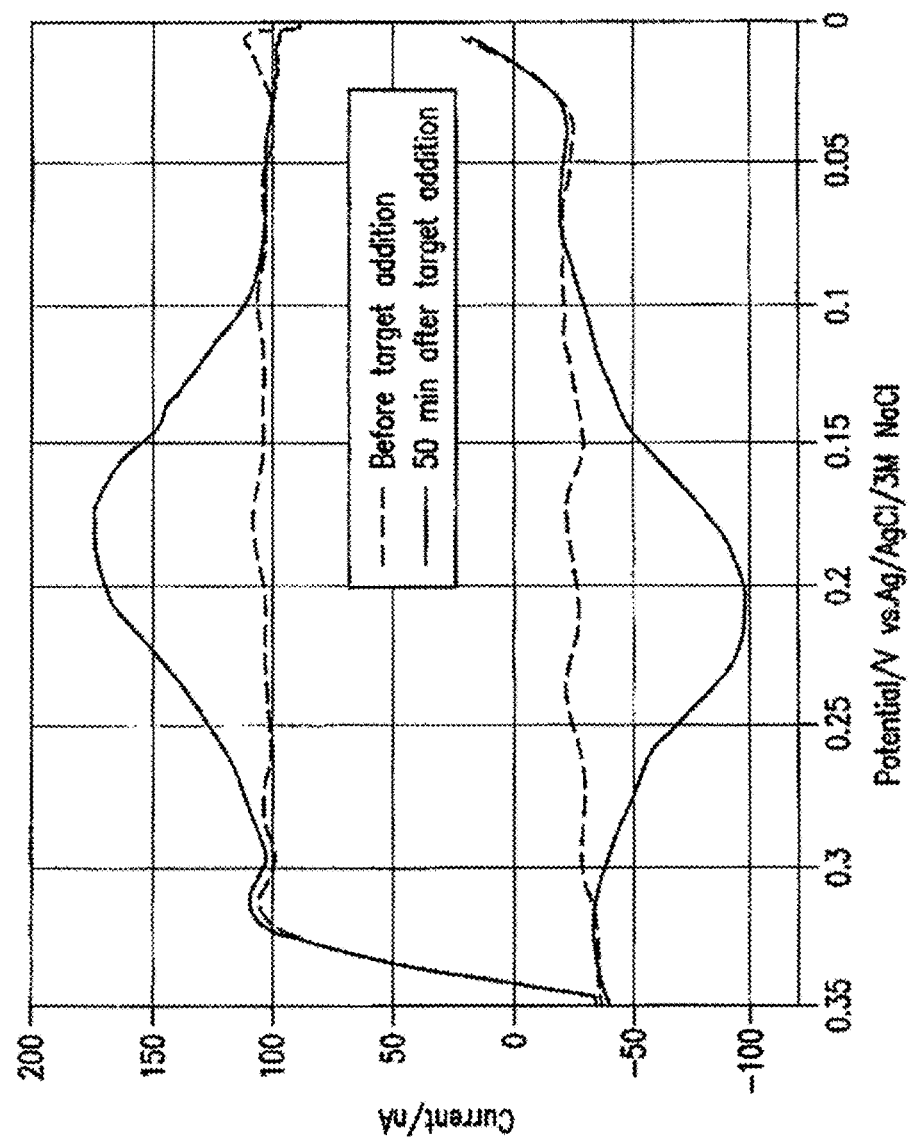
FIG. 17 depicts output according to an exemplary embodiment of the disclosed subject matter.

FIG. 17 shows output from the ADC measured at one of the 100 μm WEs in the array, functionalized with probe P1, approximately 50 min after 50 nM of target T1 is introduced to the device. The current peaks due to the Fc redox reactions are evident above the charging current level, indicating hybridization between P1 and T1. The forward and reverse charging currents differ slightly because of hysteresis. Based on the average charging current, the WE interfacial capacitance is measured to be approximately 7 μF $cm^{-2}$, which is in the range for an MCP-modified Au electrode at the exemplified DNA coverage and buffer ionic strength. The charging current, before DNA target is added to the buffer, is shown along with the sensor response from hybridization, 50 min after target addition, at one 100 μm WE.

Figure 22:
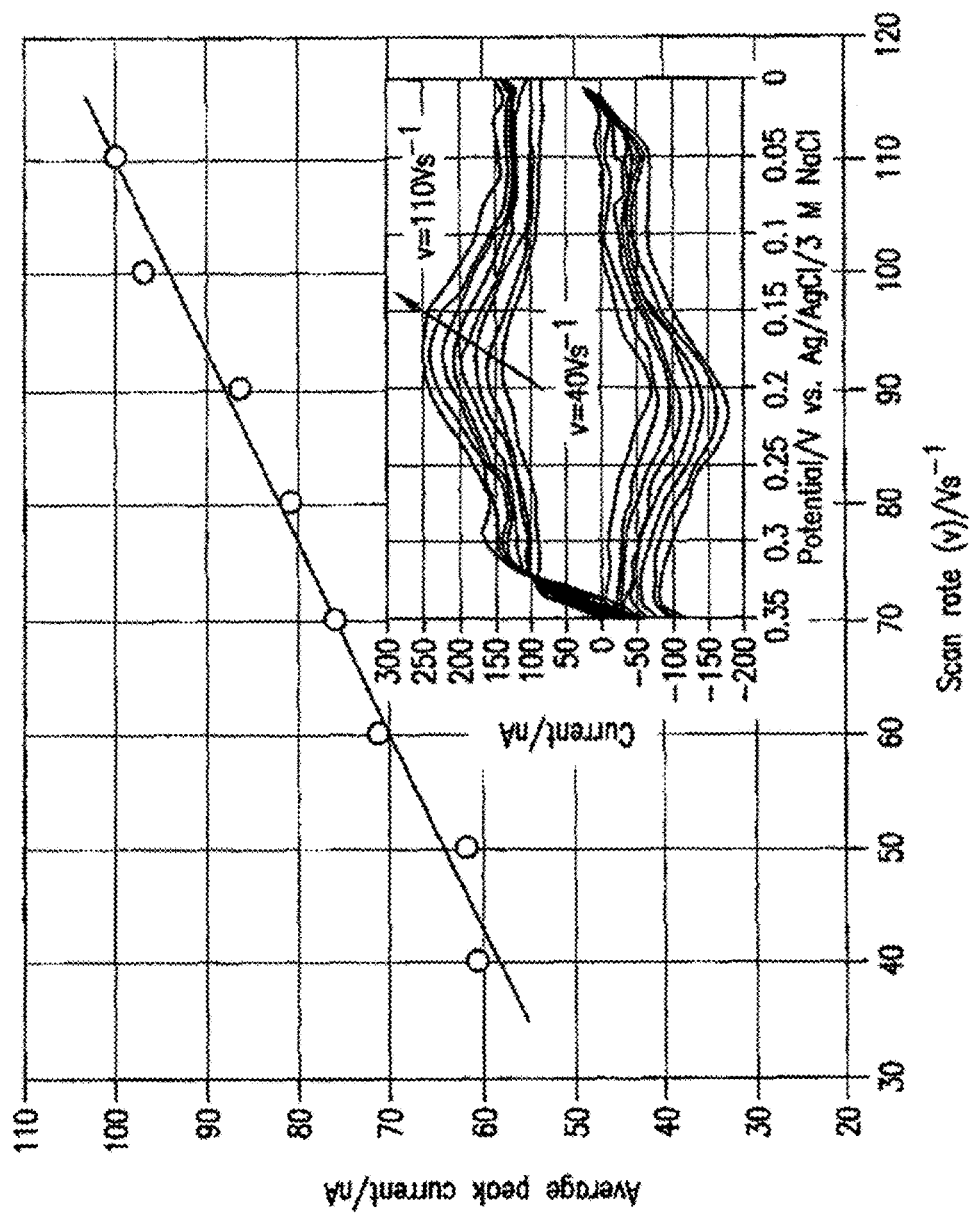
FIG. 22 depicts results according to an exemplary embodiment of the disclosed subject matter.

It can be observed in FIG. 22 that the peak current level (average of forward and reverse peaks after background subtraction) rises linearly with increasing scan rate, in accordance with theoretical principles for a surface redox species. This illustration confirms that the signal current originates from surface-hybridized targets and not diffusing species in solution. The inset shows the resulting waveform from multiple scans.

Figure 23:
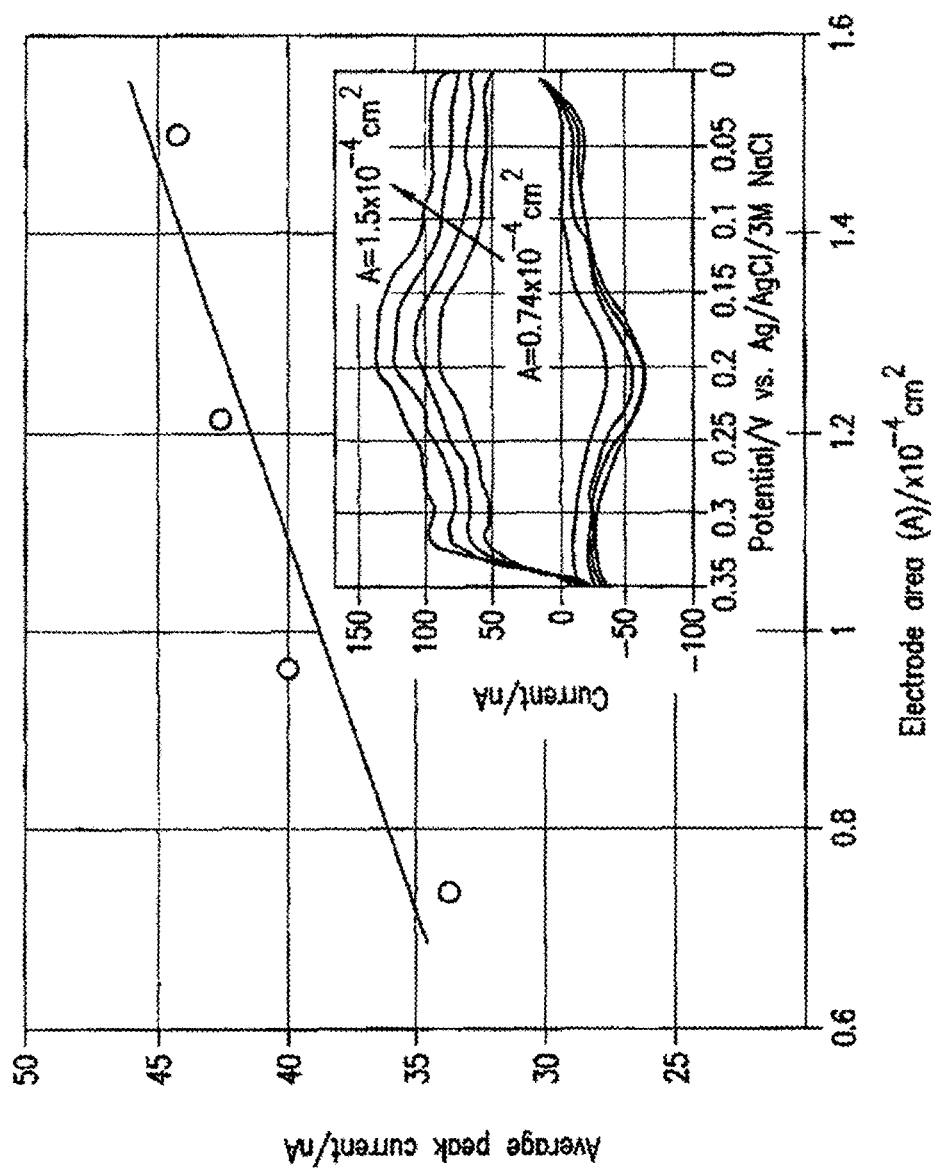
FIG. 23 depicts results according to another embodiment of the disclosed subject matter.
Figure 24:
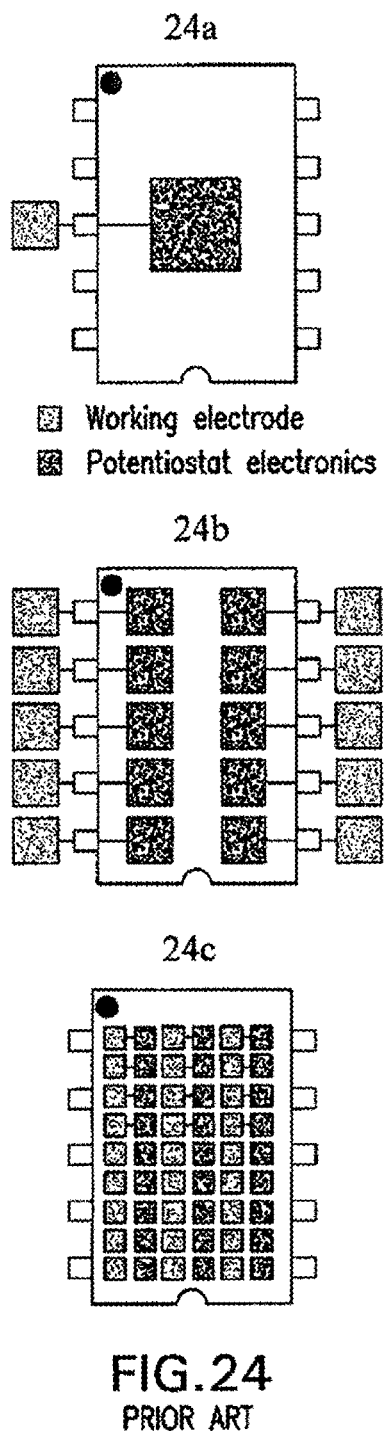
FIG. 24 depicts various CMOS sensor implementations.

It can be observed in FIG. 23 that the average peak current increases linearly as a function of electrode area, in accordance with theoretical principles. The inset shows the resulting waveform from each scan.

In embodiments where the 2.5 V supply limits the potential range over which the on-chip control amplifiers operate, the on-chip CEs can be bypassed and an external discrete operational amplifier (e.g., AD8628, available from Analog Devices, Norwood, Mass., USA), that can operate up to 3 V can be used to drive the RE and an off-chip Pt-wire CE. In other embodiments, the control amplifiers can be designed using thick-gate-oxide transistors, which can be operated up to 3.3 V in the present CMOS process.

The integrated platform enables real-time quantification of surface-hybridized targets in a multiplexed fashion, allowing large-scale optimization of parameters affecting hybridization in diagnostic assays including probe coverage, target concentration, probe and target sequence, buffer ionic strength, and temperature. The relationship between the concentration of DNA target in solution and the magnitude of the sensor output signal are described below.

Figure 18:
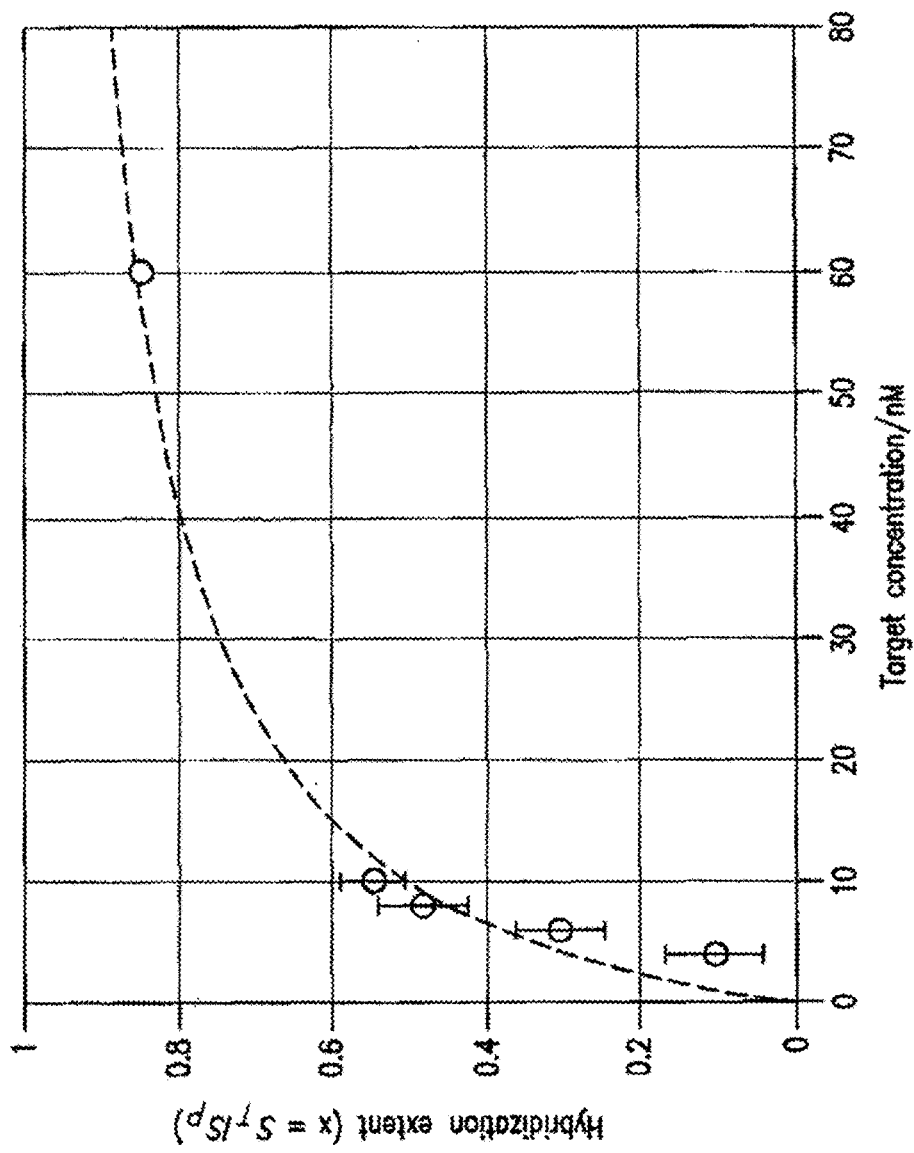
FIG. 18 depicts results according to an exemplary embodiment of the disclosed subject matter.

FIG. 18 displays the results of a target concentration series in which the hybridization extent $x=S_T/S_p$, where $S_T$ is the coverage and $S_p$ is the total probe coverage (both hybridized and non-hybridized) on the surface, is plotted as a function of the solution target concentration. The dashed line shows the Langmuir fit to this equilibrium isotherm which yields a binding constant $K_a$ of approximately $1\times10^8$ $M^{-1}$. Error bars for the four lowest target concentrations indicate the standard deviation from three separate illustrations. Assuming the kinetics of hybridization between probe P and target T to form the DNA duplex D follow the reversible reaction $$P+T \leftrightarrow D \quad (1)$$

and the reaction reaches equilibrium, the equilibrium association constant $K_a$ can be determined using $$K_a = \frac{x}{1-x}\frac{1}{C_T}, \quad (2)$$

where $C_T$ is the solution target concentration which is assumed to be much larger than that needed to fully react with the probe layer. By fitting the data in FIG. 18 according to (2), $K_a$ is found to be approximately $1\times10^8$ $M^{-1}$. This value of $K_a$ falls in the range determined in other work involving surface-based assays ($10^7$-$10^9$ M$^{-1}$).

The lowest target coverage measured using the platform of the embodiment of FIG. 18 is about 1×10$^{12}$ cm$^{-2}$ (where x=0.1 and the corresponding target concentration is 4 nM). In other embodiments, the hardware detection limit of the device is determined by the lowest measurable current. In some instances, the hardware sensitivity limit can be evaluated from electronic measurement of the dynamic range of the sensor ADCs (when operated at a 10 kHz sampling rate). Such measurements indicate that a current of 550 pA can be detected with a signal-to-noise ratio of three. This sets a detection limit of approximately 4×10$^{10}$ cm$^{-2}$ (or equivalently, a 50 pM target concentration given the calculated value of $K_a$ above) assuming the maximum redox current $I_{max}$ from the Fc reaction can be expressed using $$I_{max} = \frac{n^2 F^2}{4RT} vA\left(\frac{S_T}{N_A}\right), \tag{3}$$

which applies to surface-bound electroactive species where n is the number of electrons transferred (one for the Fc reaction), F is the Faraday constant, R is the molar gas constant, T is the absolute temperature, and v is the CV scan rate.

In some embodiments, alternative protocols for label-based detection, coupled with the implementation of a higher resolution ADC, significantly improves the detection limit of the CMOS electrochemical sensor array, simultaneously. For example, use of multiple (e.g., electroactive dendrimer) labels can be used to boost signal per hybridized target. Alternately, employing background subtractive measurement techniques such as ac voltammetry or square-wave voltammetry can be used to reduce background currents and amplify the desired current from the redox activity of the labels. Alternative protocols for label-based detection include the use of biotin-streptavidin chemistry or added intercalater molecules.

Observation of the entire hybridization process in real time allows the point at which equilibrium has been reached during hybridization to be determined unambiguously to improve assay reproducibility and sensitivity. In addition, kinetic studies of DNA binding can be carried out to provide insight into the physical processes governing affinity-based sensing. Furthermore, the additional data provided by real-time sensing allows temporal averaging of the measured signal to be performed. This improves signal-to-noise ratio by reducing the effect of independent noise sources, such as those arising from non-ideal instrumentation, as well as interfering biochemical processes such as cross-hybridization, which can become more noticeable in assays exhibiting low expression levels.

Several approaches to real-time monitoring of surface bio-affinity reactions exist. For example, surface plasmon resonance (SPR), quartz crystal microbalance (QCM), and cantilever sensors are capable of performing real-time DNA sensing. However, electrochemical sensing techniques include simpler hardware and facile CMOS integration without surface micromachining or more complex post-processing as with cantilever or QCM fabrication.

Figure 19:
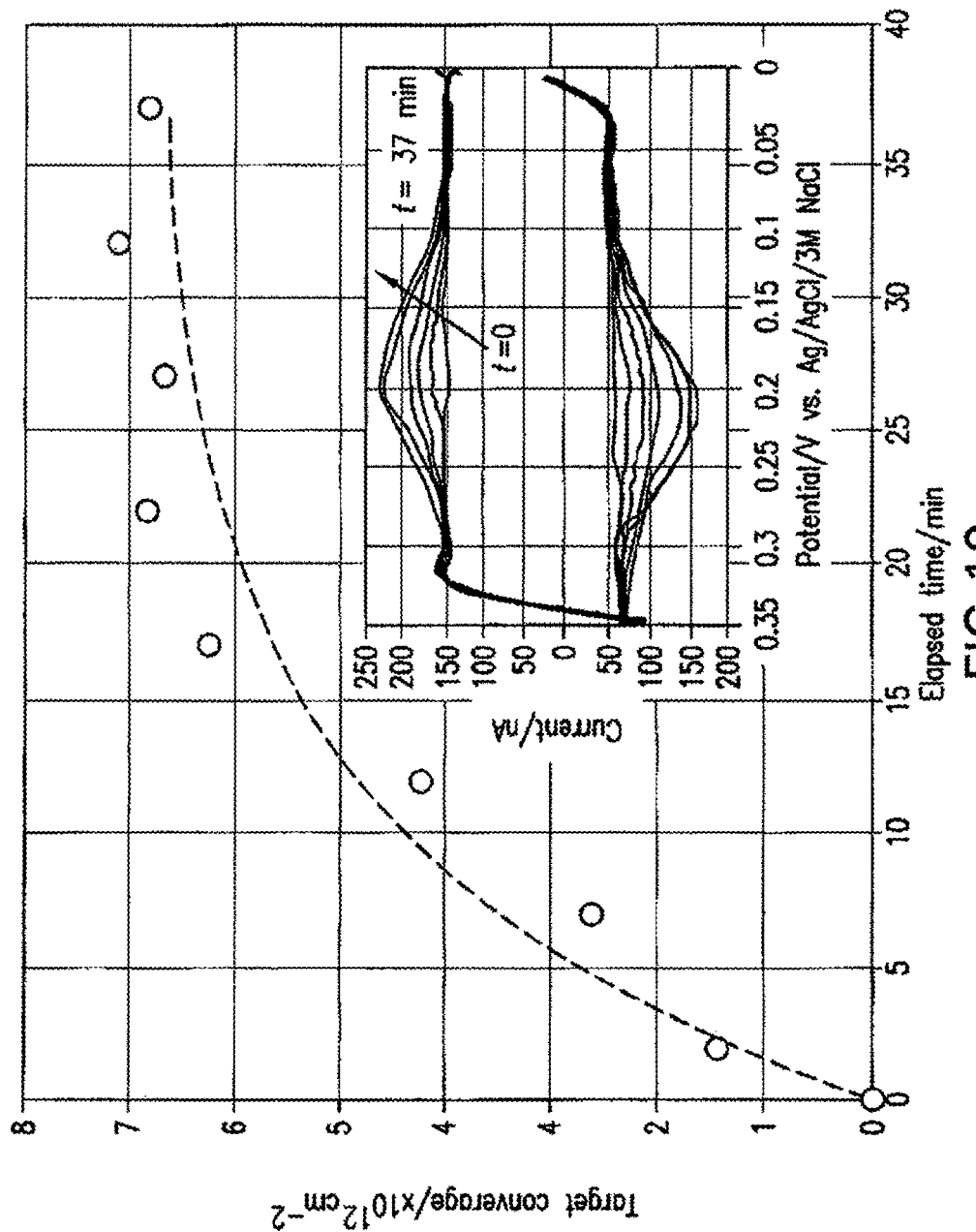
FIG. 19 depicts results according to another embodiment of the disclosed subject matter.

FIG. 19 demonstrates the measurement of real-time kinetics in one embodiment where 60 nM of T1 is hybridized to complementary P1. This CV measurement is taken at one of the 100-μm WEs, with a scan repeated every 5 minutes and the cell potential held at 0 V between scans. The measured data is fit to a first-order rate equation (dashed line) following Langmuir kinetics. Inset shows the results from each CV scan over time. An increase in the area of the redox target peak is evident over time. The maximum extent of hybridization, reached after about 35 min, is about 6.8×10$^{12}$ cm$^{-2}$.

Ignoring mass-transport limitations, effects of finite reaction volume, interactions among surface sites, and assuming that no probes have hybridized at time t=0, the coverage of DNA duplexes on the WE surface as a function of time $S_T(t)$ can be expressed as $$S_T(t) = \left(\frac{S_P C_T}{K_a^{-1} + C_T}\right)\left[1 - \exp\left(\frac{-t}{\tau}\right)\right]. \tag{4}$$

The time constant τ over which the device reaches equilibrium is given by $$\tau = \frac{1}{k_f(C_T + K_a^{-1})}. \tag{5}$$

where the forward rate constant $k_f$ and reverse rate constant $k_r$ are taken to be related by $K_a = k_f/k_r$. Performing a non-linear, least-squares fit of the real-time curve using (4) and (5) (also plotted in FIG. 5) gives a τ of about 590 s. From this, and using the value of $K_a$ determined previously, $k_f$ and $k_r$ are calculated to be 2.4×10$^4$ M$^{-1}$ s$^{-1}$ and 2.4×10$^{-4}$ s$^{-1}$, respectively. Although these results fall in the same order of magnitude as rate constants measured by others using QCM and surface plasmon fluorescence spectroscopy techniques, the measured value of $K_a$ is relatively smaller, likely because avidin-biotin spacers were used for probe immobilization in the referenced works.

In some embodiments, multiplexed and specific detection are accomplished using the CMOS biosensor array by functionalizing the chip with two distinct probes and hybridizing each with its complementary target. Probes P1 and P2 are spotted on four different WEs each using a fluid micro-injection device (e.g., 1M-300, available from Narishige, East Meadow, N.Y., USA) capable of delivering nanoliter volumes of probe solution to the electrode surface. Initially, 6 nM of target T1, complementary to probe P1, is introduced, and FIG. 22 shows the response at one of the 100 μm WEs functionalized with P1 (denoted "site A") after 60 min. A distinct current peak indicates that hybridization has occurred. The remaining WEs functionalized with P1 show similar behavior. Conversely, those WEs on which P2 is immobilized do not exhibit a hybridization signal, as P2 and T1 have little affinity for one another. The output from the sensor at one of the 100-μm WEs functionalized with P2 (denoted "site B") is also displayed in FIG. 20.

Figure 20:
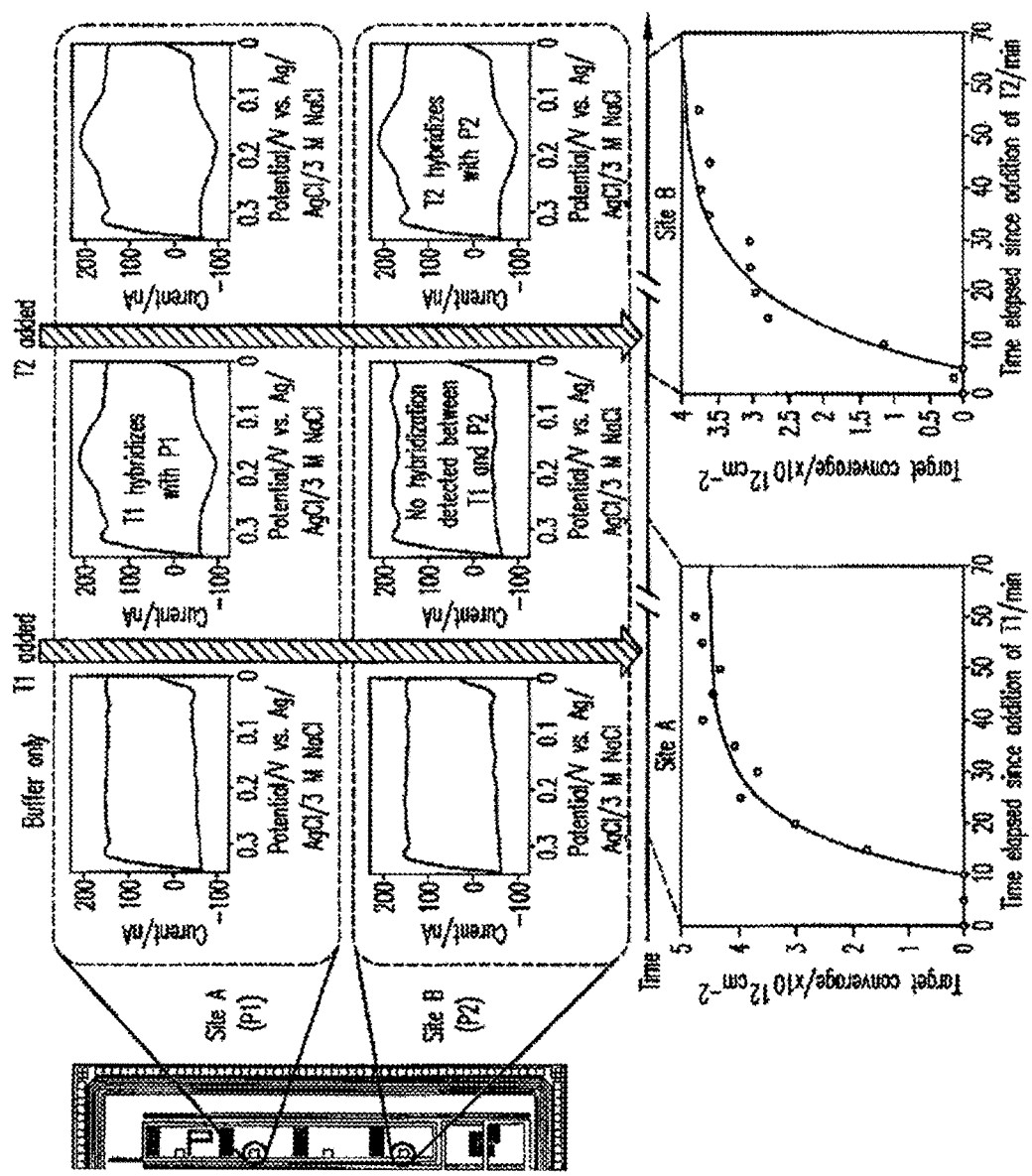
FIG. 20 depicts results according to yet another embodiment of the disclosed subject matter.

Next, 6 nM of target T2 is introduced. After 55 min, the hybridization signal at site B is evident, as shown in FIG. 20. The signal at site A (measured at the same time) has not changed, however, since T1 is still present in solution. A separate experiment confirmed that sites functionalized with P1 do not exhibit any hybridization when T2 is added to the buffer first.

FIG. 20 also shows the measured target coverages at sites A and B as a function of time elapsed since target addition. The values of τ for the hybridization processes are approximately 540 s and 740 s at site A and B, respectively. The slight shift of the data relative to the origin is attributed to mass-transport limitations at the early times of hybridization. These data demonstrate that the biosensor platform is capable of performing real-time monitoring of DNA hybridization in a multiplexed fashion.

Figure 14A:
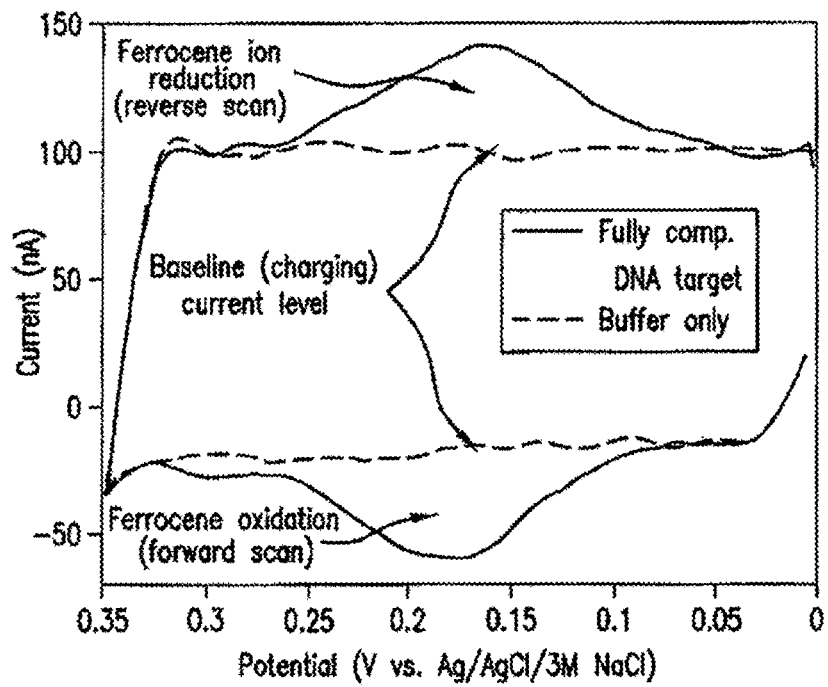
FIGS. 14a and 14b depict results according to further embodiments of the disclosed subject matter.

In some embodiments, the chip is cleaned as described previously and is then incubated in a 0.50-µM solution of 20-mer DNA probe, followed by incubation in MCP. The sensor array is operated in 1-M PPB and the baseline current level at a 100-µm WE is first measured as shown in FIG. 14a.

A solution of Fc-labeled target DNA, having a sequence of DNA bases that is fully-complementary to that of the probe, is added to the electrolyte so that the overall target concentration is 6 nM. After 60 min the signal stabilizes and current peaks are evident from the Fc-labeled targets that have bound to the probes, as shown in FIG. 14a. Based on the area enclosed by the redox signal and baseline current, the surface density of hybridized target is $4.55 \times 10^{12}$ cm$^{-2}$.

Figure 14B:
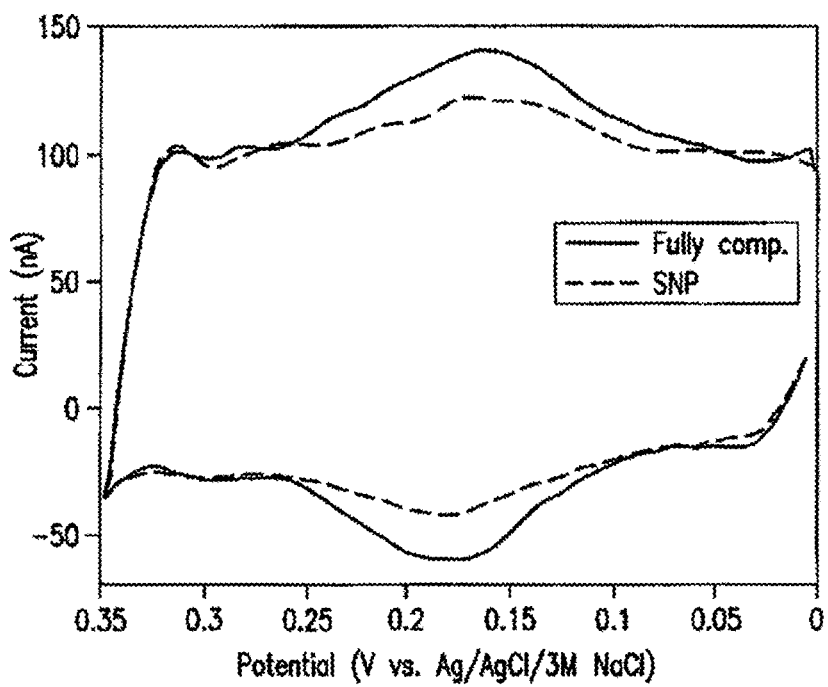

In another example embodiment, the same procedure as above is followed; however, a DNA-target sequence having a single-base mismatch compared to the probe is used. Sensor specificity in the presence of these single-nucleotide polymorphisms (SNPs) can be useful for genetic testing, in which mutations are characterized by single (or few) base-pair changes. FIG. 14b displays the resulting CV curve using the single-mismatch target sequence along with the curve obtained from the fully-complementary target for comparison. Because the target containing the SNP has less affinity for the probe, a smaller fraction of probe is hybridized, as can be seen from the reduced signal level in the figure. The density of hybridized probe and target in this case is $2.38 \times 10^{12}$ cm$^{-2}$.

In some embodiments, the density of the current CMOS biosensor array is approximately 250 cm$^{-2}$. In other embodiments, the density can be increased to more than 6000 cm$^{-2}$ for the same 100 µm×100 µm WE area by optimizing the physical layout of the on-chip electronics. This density would be comparable to existing, commercial detection devices, while additionally incorporating the full potentiostat sensing electronics on chip not present in the commercial devices.

In other embodiments, the CMOS biosensor array can be used in clinical gene expression samples that have traditionally been analyzed with fluorescence-based arrays.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within the spirit and scope thereof.

The invention claimed is:

1. A system for electrochemical sensing of biomolecules, comprising:
   an integrated circuit;
   one or more working electrodes on the integrated circuit, the one or more working electrodes configured to receive one or more biomolecular probes, a desired potential maintained through one or more reference electrodes, the one or more working electrodes configured to form a portion of one or more corresponding potentiostats, the one or more working electrodes being arranged in a plurality of rows, wherein each row of the one or more working electrodes shares a corresponding counter electrode that is being driven by a respective control amplifier; and
   an analog-to-digital converter circuit on the integrated circuit configured to measure a signal indicative of a biomolecule sensing operation in real time.

2. The system of claim 1, wherein the integrated circuit is a complementary metal-oxide-semiconductor (CMOS) chip comprising a top metal layer operably connected to one or more vias for routing electrical signals.

3. The system of claim 2, wherein the chip is fabricated in a 2.5-V, 5-metal, 0.25-µm CMOS process.

4. The system of claim 1, wherein the one or more working electrodes comprise square, gold electrodes.

5. The system of claim 2, wherein the one or more working electrodes are adhered to the top metal layer with an adhesion layer.

6. The system of claim 5, wherein the adhesion layer comprises titanium.

7. The system of claim 1, wherein the analog-to-digital converter circuit is a dual-slope analog-to-digital converter circuit.

8. The system of claim 1, wherein the one or more working electrodes are in contact with an electrolyte solution, and the electrolyte solution includes one or more target molecules.

9. A system for electrochemical sensing of biomolecules, comprising:
   one or more biomolecular probes configured to be bound to one or more working electrodes of an integrated circuit, the integrated circuit including the one or more working electrodes, a desired potential maintained through one or more reference electrodes, and an analog-to-digital converter circuit on the integrated circuit configured to measure a signal indicative of a biomolecule sensing operation in real time, the one or more working electrodes configured to form a portion of one or more corresponding potentiostats, the one or more working electrodes being arranged in a plurality of rows, wherein each row of the one or more working electrodes shares a corresponding counter electrode that is being driven by a respective control amplifier; and
   a measurement arrangement configured to perform an electrochemical measurement operation to measure one or more aspects of a biomolecular reaction in real time.

10. The system of claim 9, wherein the integrated circuit is a complementary metal-oxide-semiconductor (CMOS) chip comprising a top metal layer operably connected to one or more vias for routing electrical signals.

11. The system of claim 9, wherein the electrochemical measurement operation includes cyclic voltammetry, linear-sweep voltammetry, square-wave voltammetry, ac voltammetry, ac impedance, or electrochemical impedance spectroscopy techniques.

12. The system of claim 9, further comprising:
   analyzing the biomolecular reaction to quantify surface target coverages.

13. A system for electrochemical sensing of biomolecules, comprising:
   an integrated circuit;
   one or more working electrodes on the integrated circuit, the one or more working electrodes configured to receive one or more biomolecular probes, a desired potential maintained through one or more reference electrodes, the one or more working electrodes configured to form a portion of one or more corresponding potentiostats, the one or more working electrodes being arranged in a plurality of rows, wherein each row of the one or more working electrodes is associated with a different length, and wherein each row of the one or more working electrodes shares a corresponding counter electrode that is being driven by a respective control amplifier; and
an analog-to-digital converter circuit on the integrated circuit configured to measure a signal indicative of a biomolecule sensing operation in real time.

* * * * *